US008214007B2

(12) United States Patent
Baker et al.

(10) Patent No.: US 8,214,007 B2
(45) Date of Patent: Jul. 3, 2012

(54) BODY WORN PHYSIOLOGICAL SENSOR DEVICE HAVING A DISPOSABLE ELECTRODE MODULE

(75) Inventors: Steven D. Baker, Beaverton, OR (US); Eric T. McAdams, Whitehead (GB); James P. Welch, Laguna Niguel, CA (US); Norbert Ohlenbusch, Andover, MA (US); Thomas P. Blackadar, Natick, MA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 491 days.

(21) Appl. No.: 11/591,619

(22) Filed: Nov. 1, 2006

(65) Prior Publication Data

US 2008/0139953 A1    Jun. 12, 2008

(51) Int. Cl.
*A61N 1/00* (2006.01)
*A61B 5/04* (2006.01)
(52) U.S. Cl. .......... 600/372; 607/60; 600/382; 600/509
(58) Field of Classification Search .................... 607/60; 600/372, 382, 509
See application file for complete search history.

(56) References Cited

U.S. PATENT DOCUMENTS

| | | |
|---|---|---|
| 4,141,367 A | 2/1979 | Ferreira |
| 4,791,933 A | 12/1988 | Asai et al. |
| 4,800,894 A | 1/1989 | Milani |
| 4,957,109 A | 9/1990 | Groeger et al. |
| 4,958,645 A | 9/1990 | Cadell et al. |
| 4,974,607 A | 12/1990 | Miwa |
| 5,257,631 A | 11/1993 | Wik |
| 5,294,928 A * | 3/1994 | Cooper et al. ............... 341/142 |
| 5,309,918 A * | 5/1994 | Schraag ........................ 600/508 |
| 5,319,363 A | 6/1994 | Welch et al. |
| 5,458,122 A | 10/1995 | Hethuin |
| 5,515,735 A | 5/1996 | Sarihan |
| 5,538,007 A | 7/1996 | Gorman |
| 5,544,661 A | 8/1996 | Davis et al. |
| 5,579,001 A | 11/1996 | Dempsey et al. |

(Continued)

FOREIGN PATENT DOCUMENTS

EP    0209804 A2    1/1987

(Continued)

OTHER PUBLICATIONS

Japanese Office Action dated Jan. 12, 2010 for Japanese Patent Application No. 2006-507455 (5 pages).

*Primary Examiner* — Nicole F Lavert
(74) *Attorney, Agent, or Firm* — Sonny Z. Zhan

(57) ABSTRACT

A body worn patient monitoring device includes at least one disposable module including a plurality of electrical connections to the body. The body worn patient monitoring device also includes at least one communication-computation module, the communication-computation module having at least one microprocessor to actively monitor the patient and to perform a real-time physiological analysis of the physiological signals. A radio circuit communicates a raw physiological signal or a result of the physiological analysis at a predetermined time or on the occurrence of a predetermined event, via a radio transmission to a remote radio receiver, wherein the at least one disposable module is mechanically and electrically coupled directly to the at least one communication-computation module. The body worn patient monitoring device, including the at least one disposable module and the at least one communication-computation module, is directly non-permanently affixed to the skin surface of the patient.

45 Claims, 14 Drawing Sheets

U.S. PATENT DOCUMENTS

| | | |
|---|---|---|
| 5,579,775 A | 12/1996 | Dempsey et al. |
| 5,600,071 A | 2/1997 | Sooriakumar et al. |
| 5,682,803 A | 11/1997 | Boianjiu |
| 5,687,734 A | 11/1997 | Dempsey et al. |
| 5,694,940 A | 12/1997 | Unger et al. |
| 5,743,269 A | 4/1998 | Okigami et al. |
| 5,748,103 A | 5/1998 | Flach et al. |
| 5,767,791 A | 6/1998 | Stoop et al. |
| 5,808,331 A | 9/1998 | Zhang et al. |
| 5,832,490 A | 11/1998 | Riley |
| 5,871,451 A | 2/1999 | Unger et al. |
| 5,882,300 A | 3/1999 | Malinouskas et al. |
| 5,889,211 A | 3/1999 | Maudie et al. |
| 5,899,866 A | 5/1999 | Cyrus et al. |
| 5,916,159 A | 6/1999 | Kelly et al. |
| 5,917,414 A | 6/1999 | Oppelt et al. |
| 5,919,141 A | 7/1999 | Money et al. |
| 5,938,597 A | 8/1999 | Stratbucker |
| 5,966,692 A | 10/1999 | Langer et al. |
| 5,987,519 A | 11/1999 | Peifer et al. |
| 5,995,861 A | 11/1999 | Price |
| 6,006,125 A | 12/1999 | Kelly et al. |
| 6,013,933 A | 1/2000 | Foerstner et al. |
| 6,018,705 A | 1/2000 | Gaudet et al. |
| 6,026,321 A | 2/2000 | Miyata et al. |
| 6,052,654 A | 4/2000 | Gaudet et al. |
| 6,057,758 A | 5/2000 | Dempsey et al. |
| 6,066,093 A | 5/2000 | Kelly et al. |
| 6,073,046 A | 6/2000 | Patel et al. |
| 6,076,003 A | 6/2000 | Rogel |
| 6,089,692 A | 7/2000 | Anagnostopoulos |
| 6,122,340 A | 9/2000 | Darley et al. |
| 6,150,951 A | 11/2000 | Olejniczak |
| 6,161,036 A | 12/2000 | Matsumura et al. |
| 6,171,237 B1 | 1/2001 | Avitall et al. |
| 6,198,394 B1 | 3/2001 | Jacobsen et al. |
| 6,212,944 B1 | 4/2001 | Kwun et al. |
| 6,298,314 B1 | 10/2001 | Blackadar et al. |
| 6,331,444 B1 | 12/2001 | Ferrari et al. |
| 6,336,365 B1 | 1/2002 | Blackadar et al. |
| 6,357,147 B1 | 3/2002 | Darley et al. |
| 6,440,067 B1 | 8/2002 | DeLuca et al. |
| 6,448,621 B1 | 9/2002 | Thakur |
| 6,493,652 B1 | 12/2002 | Ohlenbusch et al. |
| 6,539,613 B1 * | 4/2003 | Ulmer ............................ 29/620 |
| 6,544,171 B2 | 4/2003 | Beetz et al. |
| 6,544,173 B2 | 4/2003 | West et al. |
| 6,544,174 B2 | 4/2003 | West et al. |
| 6,579,231 B1 | 6/2003 | Phipps |
| 6,586,810 B2 | 7/2003 | Thakur |
| 6,623,312 B2 * | 9/2003 | Merry et al. ................... 439/729 |
| 6,794,990 B2 | 9/2004 | Tseng |
| 6,847,892 B2 | 1/2005 | Zhou et al. |
| 6,870,484 B1 | 3/2005 | Brinsfield et al. |
| 6,911,727 B1 | 6/2005 | Martin et al. |
| 7,318,417 B2 | 1/2008 | Lang et al. |
| 7,382,247 B2 | 6/2008 | Welch et al. |
| 7,439,856 B2 | 10/2008 | Weiner et al. |
| 7,508,064 B2 | 3/2009 | Martin et al. |
| 7,515,043 B2 | 4/2009 | Welch et al. |
| 7,515,044 B2 | 4/2009 | Welch et al. |
| 7,563,632 B2 | 7/2009 | Martin et al. |
| 2001/0023315 A1 | 9/2001 | Flach et al. |
| 2002/0106709 A1 * | 8/2002 | Potts et al. ........................ 435/14 |
| 2002/0122519 A1 * | 9/2002 | Douglas et al. ................ 375/376 |
| 2003/0001742 A1 * | 1/2003 | Eshelman et al. .......... 340/573.1 |
| 2003/0055460 A1 * | 3/2003 | Owen et al. ........................ 607/5 |
| 2003/0149349 A1 | 8/2003 | Jensen |
| 2004/0113806 A1 | 6/2004 | Neykov |
| 2004/0242976 A1 * | 12/2004 | Abreu ........................... 600/315 |
| 2004/0252031 A1 | 12/2004 | Taylor |
| 2005/0116820 A1 | 6/2005 | Goldreich |
| 2005/0137489 A1 * | 6/2005 | Jackson et al. ................ 600/515 |
| 2005/0206518 A1 * | 9/2005 | Welch et al. .............. 340/539.12 |
| 2005/0216334 A1 | 9/2005 | Mehrabani-Farsi |
| 2005/0245839 A1 * | 11/2005 | Stivoric et al. ................ 600/549 |
| 2006/0044856 A1 * | 3/2006 | Bird et al. ...................... 363/131 |
| 2006/0074284 A1 * | 4/2006 | Juola et al. .................... 600/372 |
| 2006/0136001 A1 * | 6/2006 | Ortega et al. ....................... 607/9 |
| 2006/0183434 A1 * | 8/2006 | Westra et al. ..................... 455/78 |
| 2006/0189976 A1 * | 8/2006 | Karni et al. ....................... 606/41 |
| 2006/0205171 A1 * | 9/2006 | Tsukada ......................... 438/382 |
| 2006/0238333 A1 | 10/2006 | Welch et al. |
| 2007/0013511 A1 | 1/2007 | Weiner et al. |
| 2007/0069887 A1 | 3/2007 | Welch et al. |
| 2007/0270678 A1 * | 11/2007 | Fadem et al. .................. 600/372 |
| 2007/0293781 A1 | 12/2007 | Sims et al. |
| 2009/0043185 A1 | 2/2009 | McAdams et al. |
| 2009/0131759 A1 | 5/2009 | Sims et al. |
| 2010/0145202 A1 | 6/2010 | McLaughlin et al. |
| 2010/0160762 A1 | 6/2010 | McLaughlin et al. |
| 2010/0324390 A1 | 12/2010 | McLaughlin et al. |

FOREIGN PATENT DOCUMENTS

| | | |
|---|---|---|
| EP | 0770349 A1 | 5/1997 |
| EP | 0910985 A1 | 4/1999 |
| JP | 11042214 | 2/1999 |
| JP | 11-088546 | 3/1999 |
| WO | WO 9620641 A1 | 7/1996 |
| WO | WO 9629005 A1 | 9/1996 |
| WO | WO 9746156 A1 | 12/1997 |
| WO | WO 9959460 A2 | 11/1999 |
| WO | WO 01/89362 A2 | 11/2001 |
| WO | WO 01/89362 A3 | 11/2001 |
| WO | WO 01/97686 A1 | 12/2001 |
| WO | WO 2008/142365 | 11/2008 |
| WO | WO 2009/056859 | 5/2009 |

* cited by examiner

BODY WORN PHYSIOLOGICAL SENSOR DEVICE HAVING A DISPOSABLE ELECTRODE MODULE

FIELD OF THE INVENTION

This invention relates generally to a physiological monitor and more particularly to a body worn physiological monitor.

BACKGROUND OF THE INVENTION

Measurements of various physiological parameters are important to the study of the human condition. Physiological measurements can be particularly important in a health care setting, such as in a hospital. One of the more important physiological measurements performed on a patient is the electrocardiogram (ECG), showing the condition of the human heart.

Portable patient monitors have evolved that allow patients to enjoy at least some mobility. Typically a battery operated monitor can be hung on a belt, shoulder strap, or carried by a patient using some other similar hanging arrangement. Sensors, such as ECG electrodes, are affixed to the patient's body, such as with tape, and connected to the battery operated monitor by wires. After a fixed interval of time, or at a low battery indication, the batteries can be replaced or recharged. One example of a portable patient monitor is the Micropaq wireless patient monitor, manufactured by Welch Allyn, Inc., that permits multi-parameter monitoring and patient alarm capabilities built in a small, rugged, lightweight, patient-wearable device.

Another version of a portable physiological monitor is the heart rate monitor typically used by individuals engaged in an athletic activity. The monitor includes a sensor, which generally makes direct or indirect contact with an individual's chest to monitor heart beats and then by wires, or by wireless techniques, the sensor transmits the sensed heart beat to a nearby microcomputer based monitor and display. Such units generally measure only heart beat and are not capable of doing any of the traditional ECG analysis functions.

A recurrent problem with the portable monitors typically used in healthcare applications is the need for wires from sensors situated on the patient's body to the portable unit. These wires can become tangled and cause discomfort or become unplugged when inadvertently pulled or tugged on. In addition, wire motion can increase ECG noise due to the triboelectric effect. Muscle movement can also increase ECG noise, due to the typical placement of ECG electrodes over major muscles. Moreover, portable monitor battery maintenance (e.g. battery recharging or replacement) can be time consuming and costly.

Another problem is related to the requirement that a medical grade monitor survive multiple defibrillation cycles of at least 360 joules. Conventionally, this requirement has been met by one or more power resistors situated in series with the wire leads of a fixed or portable physiological monitor. The problem is that the physical volume of conventional power resistors is too large for use in a compact monitor application.

Another shortcoming of small sensor devices is that these devices lack the intelligence to vary the amount and type of data transmitted, depending on patient condition. Exercise heart monitors do not transmit a full patient waveform for clinical analysis while medical monitors measure and transmit the full patient waveform, even when the patient is healthy. While transmitting the full patient waveform is the preferred solution from a purely clinical standpoint, such transmission requires significant power to transmit large amounts of data and restricts the design from being small and inexpensive.

Yet another problem is that arrhythmia analysis is a computationally intensive operation not well-suited to existing small portable monitors that presently have no ability to perform arrhythmia analysis.

Therefore, there is a need for a body worn combined physiological sensor and monitor having a disposable sensor, but used and worn by a patient as a single unit directly and non-permanently affixed to a patient's body. Also, what is needed is a physically compact resistive element for protecting a body worn device from damage caused by multiple defibrillation cycles. Also, what is needed is a medical-grade monitor that can intelligently measure and transmit data only as required to alert clinicians that the patient needs additional attention. What is also needed is a body-worn device capable of running arrhythmia analysis through computationally efficient algorithms.

SUMMARY OF THE INVENTION

According to one aspect, a body worn patient monitoring device comprises at least one disposable module including a plurality of electrical connections to the body. The electrical connections are coupled to a skin surface of the patient to measure physiological signals of the patient. The at least one disposable module includes a disposable module connector. The body worn patient monitoring device includes at least one internal or external power source to power the body worn patient monitoring device. The body worn patient monitoring device also includes at least one communication-computation module, having a communication-computation module connector to receive physiological signals from the at least one disposable module via said disposable module connector. The communication-computation module also includes at least one microprocessor to actively monitor the patient and to perform a real-time physiological analysis of the physiological signals and a radio circuit to communicate a raw physiological signal or a result of the physiological analysis at a predetermined time or on the occurrence of a predetermined event, via a radio transmission to a remote radio receiver, wherein the at least one disposable module is mechanically and electrically coupled directly to the at least one communication-computation module. The body worn patient monitoring device, including the at least one disposable module and the at least one communication-computation module, is directly non-permanently affixed to the skin surface of the patient.

According to another aspect, a method of providing high voltage circuit protection for a body worn monitor comprises the steps of: providing a substrate that supports one or more electrical connections to a patient's body; determining a print pattern and thickness of a first material having a first resistivity to be printed on the substrate; determining a print pattern and thickness of a second material having a second resistivity to be printed on the substrate; printing the first material onto the substrate; and printing the second material onto the substrate wherein at least part of the second material overlays the first material.

BRIEF DESCRIPTION OF THE DRAWINGS

For a further understanding of these and objects of the invention, reference will be made to the following Detailed Description which is to be read in connection with the accompanying drawings, in which.

Package styling varies slightly between the drawings. Such minor differences, e.g. the case styling of computation and communication module 102, illustrate minor variations in mechanical packaging suitable for use as body worn monitors. Drawings are not necessarily shown to scale.

DETAILED DESCRIPTION

A "body worn" device is described herein with regard to certain exemplary embodiments. A "body worn" device is defined herein as a device that is directly, but non-permanently, affixed to a patient's body. A "body worn monitor" is a device that can be directly "worn" on the patient's body as a single unit, including one or more physiological sensors and a communications and computation module to perform at least initial processing of one or more physiological measurements made using one or more physiological sensors. Unlike prior art patient-wearable devices, at least one sensor can be incorporated into the device that makes a direct or indirect (such as by capacitive coupling) electrical connection with the patient's body without the use of external wires from sensors to the device. In addition and unlike athletic heart monitors, a "body worn" monitor can be a full functioning medical grade monitor, e.g. meeting the requirements of European Unions' Medical Device Directive and other applicable industry standards, such as EC-13 for an electrocardiograph. The body worn medical-grade monitor can include a device, for example, such as a pulse oximeter, $CO_2$ monitor, respiration monitor, or can function as an ECG monitor, incorporating physiological sensors, front end analog electronic signal conditioning circuits, and a microcomputer based computation unit with wireless reporting of measured physiological data, all contained within in a "body worn" package that can be non-permanently affixed directly to a patient's body. A body-worn medical-grade monitor can also include additional measurement capabilities beyond those mentioned here.

FIGS. 1A-1D depict various views of an exemplary body worn physiological monitor 100 having a communication and computation module 102 and a disposable electrode module 110. In this exemplary embodiment, physiological monitor 100 is designed for use as an electrocardiogram (ECG) monitor for obtaining and recording and/or transmitting ECG information, including ECG waveforms and alarms for a person, such as a patient, wearing body worn physiological monitor 100.

Figure 1A:
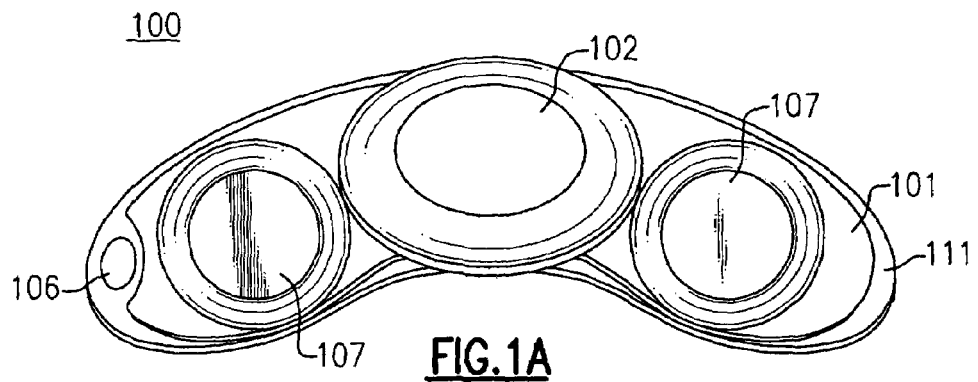
FIG. 1A shows an exemplary body worn physiological monitor having a disposable electrode module.

FIG. 1A shows an exemplary top view of body worn physiological monitor 100. A crescent shape allows the body worn physiological monitor 100 to be placed on the chest of a patient, and more specifically around the pectoralis major, to allow measurement of lead configuration I, II, or III, or to be placed on the patient's side allowing measurement using a V-lead configuration. Though not shown, multiple body worn physiological monitor 100 units can be used to effectively provide multiple leads. By placing electrodes around the body so that they are not situated directly atop major muscles, both motion noise artifacts and muscle noise artifacts can be prevented. Moreover, by eliminating cables, noise due to cable motion or compression (i.e. triboelectric effect) can be eliminated.

Figure 1B:
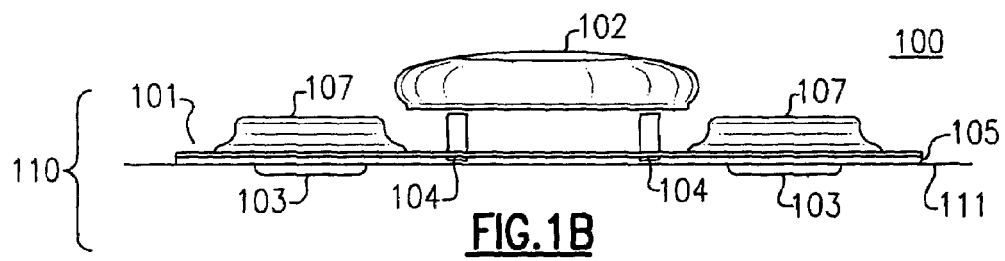
FIG. 1B shows a partially unassembled side view of the body worn physiological monitor of FIG. 1A.

FIG. 1B shows a side elevated view of physiological monitor 100 having an exemplary attachment mechanism, such as a retention clip 104, to mechanically attach communications and computation module 102 to the top surface of the disposable electrode module 110. Flexible printed circuit layer 101 can be made from a thin insulating material, such as according to this embodiment, a 75 micron thick layer of MYLAR®. Typically electrical traces (not shown in FIGS. 1A-1D) on flexible printed circuit layer 101 can be further protected by an insulating covering, analogous to a conformal coating. A formed plastic layer or a cloth with adhesive on one side thereof can be used to cover and protect flexible printed circuit layer 101, as well as to provide an aesthetic outer layer to make the body worn monitor 100 visually appealing.

Figure 1C:
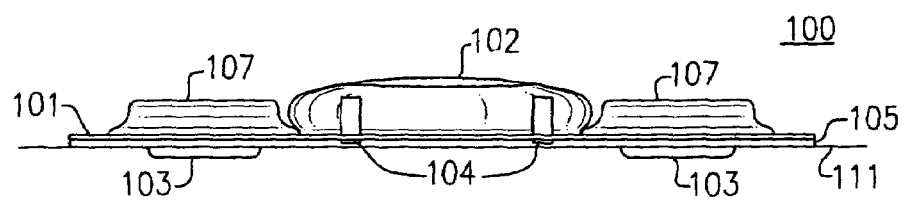
FIG. 1C shows an assembled side view of the body worn physiological monitor of FIG. 1A.
Figure 1D:
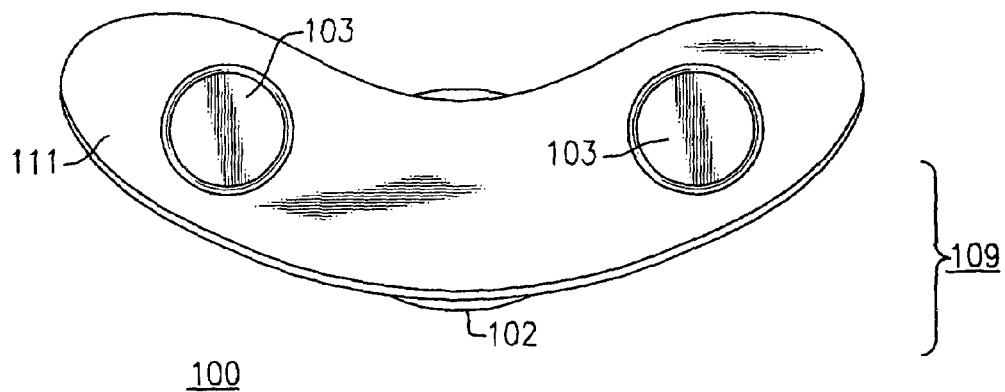
FIG. 1D shows a bottom view of the body worn physiological monitor of FIG. 1A.

FIG. 1C shows a side view of physiological monitor 100 in which the communications and computation module 102 has been affixed to disposable electrode module 110. FIG. 1D depicts a view of the underside of exemplary physiological monitor 100 showing one embodiment of disposable electrode module 110 having electrodes 109. In this embodiment, each electrode 109 comprises electrode gel 103 and conductive surface 404 (FIG. 4). Together, electrode gel 103 and conductive surface 404 create a half-cell, such as, for example, a Silver/Silver Chloride half cell. Also and according to this embodiment, conductive surface 404 can directly accept the electrode gel 103.

Figure 2:
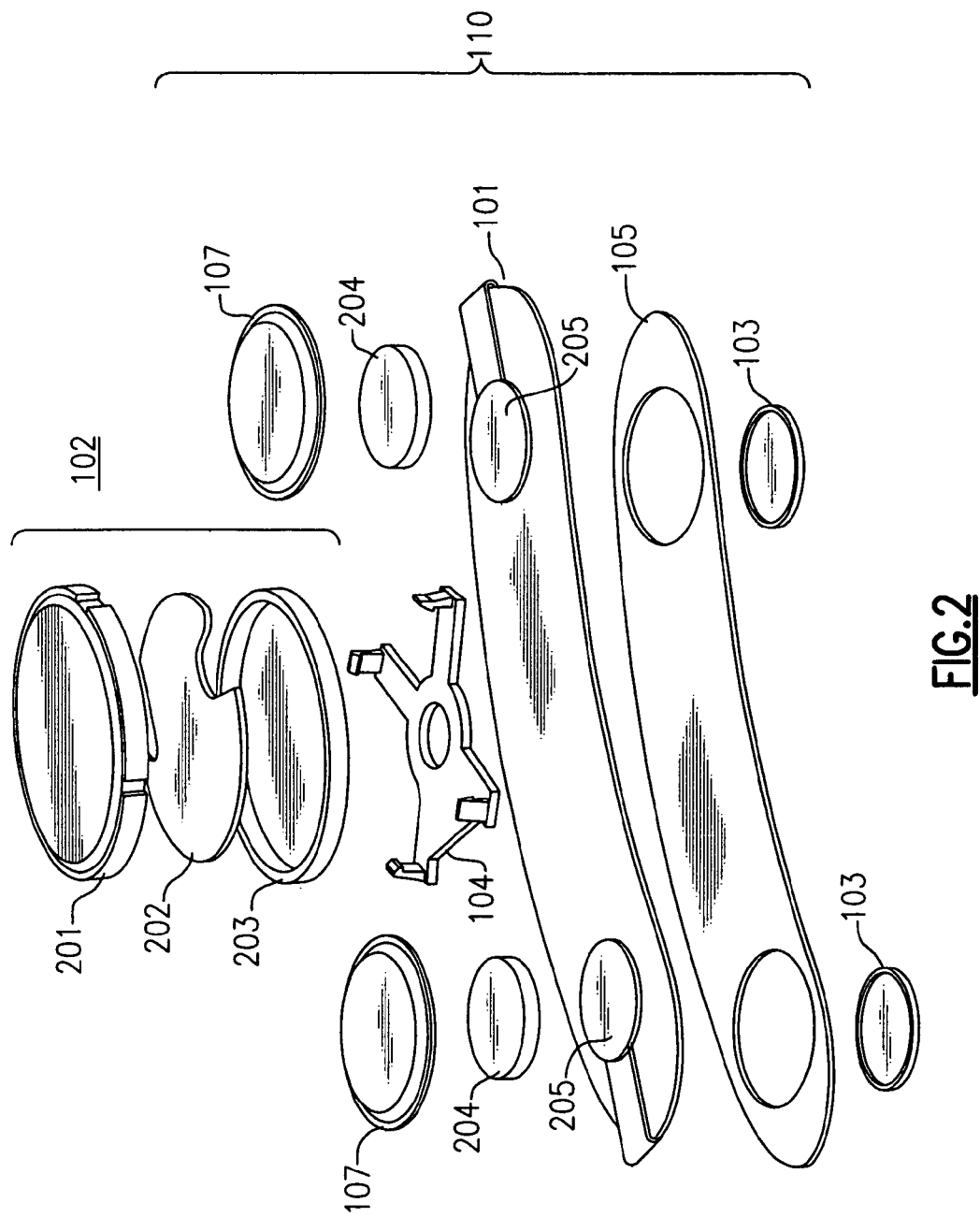
FIG. 2 shows an exploded perspective view of an exemplary body worn physiological monitor.

FIG. 2 shows an exploded assembly view of the exemplary body worn physiological monitor 100. As noted with regard to FIGS. 1A-1D, the body worn physiological monitor 100 includes a removable and reusable communications and computation module 102 and a disposable electrode module 110, the later including electrode gels 103 for ECG monitoring and batteries 204 to power communications and computation module 102. A flat planar insulating/adhesive member 105 includes a plurality of openings that are each sized to receive electrode gels 103. The insulating member 105 provides a bottom side cover for the flexible printed circuit layer 101 and augments adhesion to the human body. Electrode gel 103, when attached to an appropriate substrate such as silver-silver-chloride or other substrate, can be used to establish a relatively low impedance electrical connection between conductive surface 404 (FIG. 4) and the patient's skin.

Electrode gels 103 can adhere to a patient's skin. While electrode gel 103 is typically an adhesive electrode gel, the adhesion offered by electrode gels 103 alone might not give a sufficient holding force for non-permanently affixing body worn physiological monitor 100 to a patient. To achieve a better adhesion of body worn monitor 100 to a patient's skin, insulating/adhesive member 105 can be used to non-permanently affix body worn physiological monitor 100 to a patient. Thus, body worn monitor 100 can be applied to a patient in the same way an adhesive strip is applied, such as for example, those adhesive strips sold under the brand name "BAND-AID®". One exemplary type of foam adhesive suitable for affixing a flexible circuit board to a patient is 1.6 mm adhesive foam from Scapa Medical of Bedfordshire, UK. As shown in FIGS. 1B and 1C (although not to scale), each of the electrode gels 103 extend sufficiently below adhesive layer 105 in order to ensure good electrical connection with a patient's skin surface (not shown). Tab 106, FIG. 1A, allows for easy removal of a protective backing 111 from adhesive layer 105.

Flexible printed circuit layer 101 can include contacts, such as battery clips (not shown), to receive and connect to batteries 204. (It is contemplated that in some future embodiments, a single battery can provide sufficient electrical power.) In the exemplary embodiment, as shown in FIG. 2, batteries 204 can be mounted under respective battery flaps 205 arranged on opposite sides of the flexible printed circuit layer 101. Alternatively, battery clips (not shown) or battery holders (not shown) can be used to provide both mechanical support and electrical connections for each of the batteries 204. One type of battery holder suitable for such use, for example, is the model 2990 battery holder, manufactured by the Keystone Electronics Corp. of Astoria, N.Y. Battery cover 107 provides protection for batteries 204 as well as a surface to press upon when applying electrodes 103 to conductive surface 404. Retention clips 104 can comprise, for example, a plurality of spring fingers with latching clips. Retention clip 104, affixed to disposable electrode module 110, can be used to secure reusable communications and computation module 102 to disposable package 110. Reusable communications and computation module 102 is herein illustrated in a simplified representation, including cover 201, communications and computation printed circuit board assembly 202, and base 203.

Figure 3:
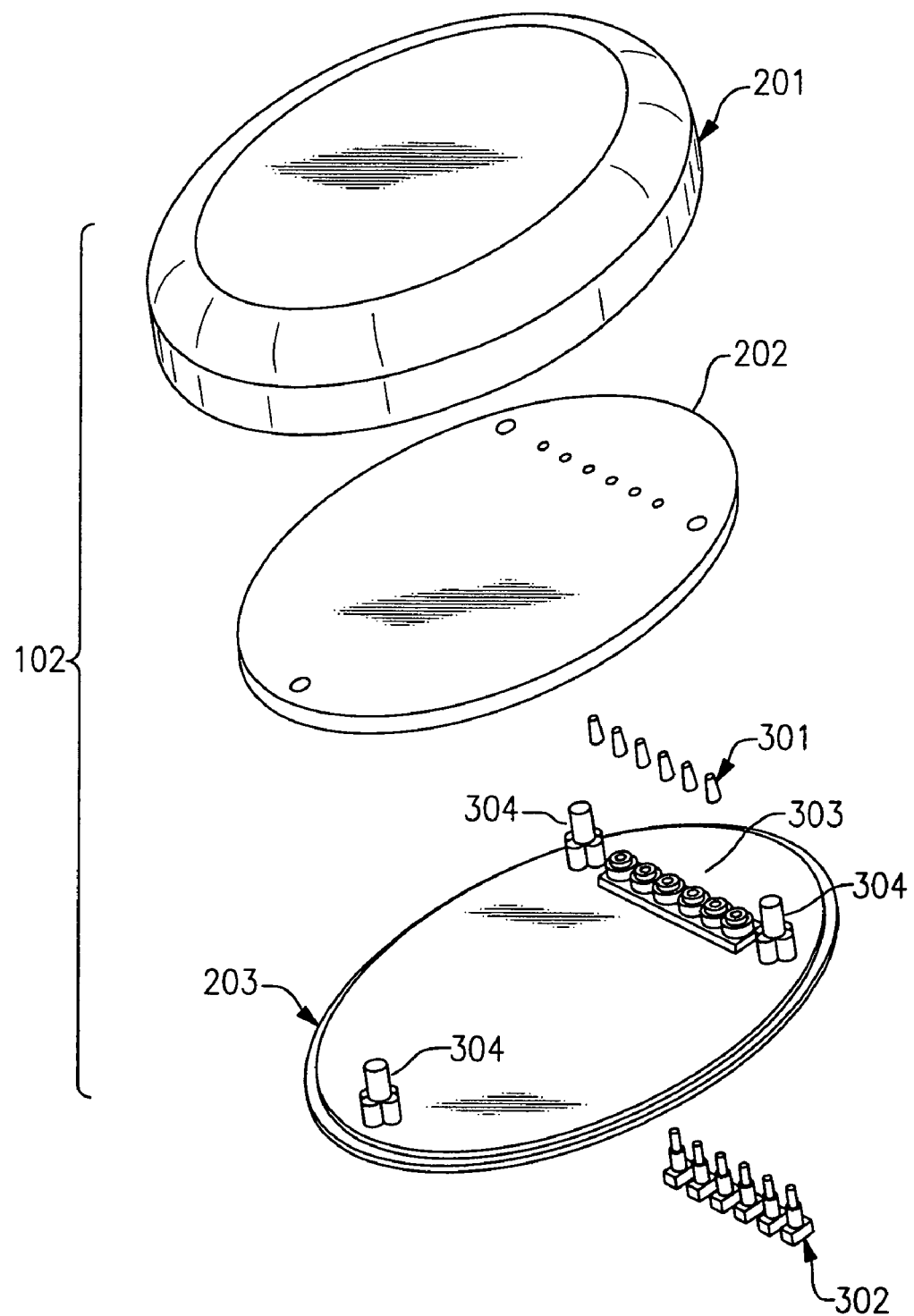
FIG. 3 shows an exploded perspective view of an exemplary computation and communication module.

FIG. 3 shows a mechanical view of an exemplary reusable communications and computation module 102, as well as a preferred method for making an electrical connection between flexible printed circuit layer 101 in disposable electrical module 110 and communications and computation printed circuit board assembly 202 situated in reusable communications and computation module 102. In this exemplary embodiment, communications and computation printed circuit board assembly 202 can include a plurality of press fit and/or soldered conductive sockets 301 for receiving electrical plug 302, the plug having a corresponding plurality of conductive pins. Each conductive pin shown in plug 302 can correspond to an electrical connection pad on flexible printed circuit layer 101. A row of mechanical sockets 303 can receive the multi-pin row of plug 302. Thus, an electrical connection can be made between each pad of flexible printed circuit layer 101 having a conductive post on plug 302 and each corresponding conductive socket 301 on communications and computation printed circuit board assembly 202. Posts 304 can align and secure each of the cover 201, communications and computation printed circuit board assembly 202, and base 203. Note that in FIG. 3, a simplified drawing of cover 201 omits slots to receive retention clip 104 to affix communications and computation module 102 to disposable package 110. A body worn monitor 100 would typically also include retention clip 104 FIG. 2, or other suitable type of mechanical clip(s), in order to provide a secure mechanical connection between communications and computation module 102 and disposable electrode module 110.

Figure 4A:
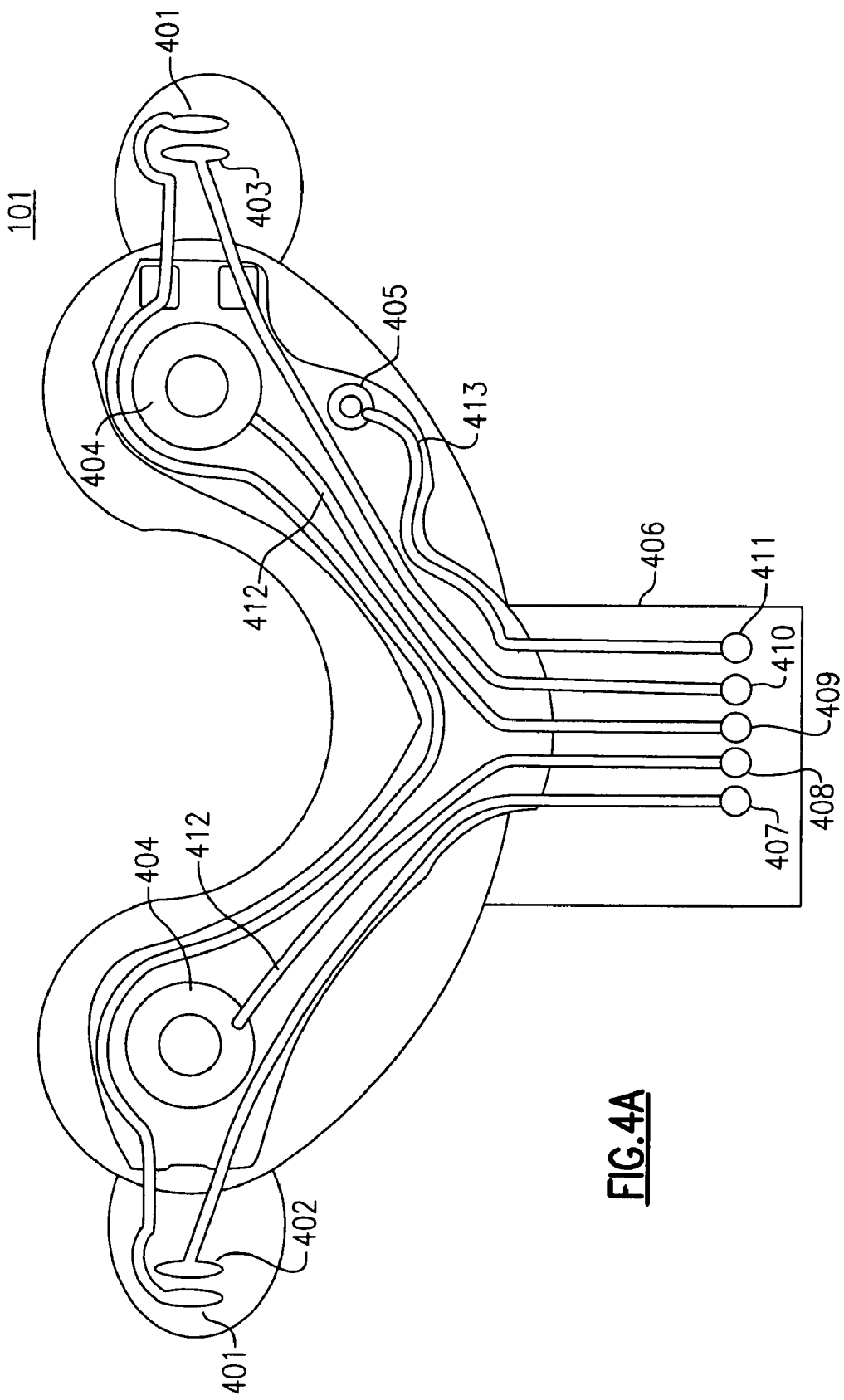
FIG. 4A shows an exemplary disposable unit flexible circuit board.

FIG. 4A shows one embodiment of flexible circuit board 101 in an expanded (e.g. unassembled view. Flexible circuit board 101 is formed on a substrate 406. Substrate 406 can be cut, for example, from MYLAR® sheet of suitable thickness. In this embodiment, one battery 204 can be mounted adjacent to an conductive surface 404. Conductive gel 103 (not shown in FIG. 4) can be mounted on the exposed conductive side of a conductive surface 404.

Conductive surface 404 can also be viewed as the electrode portion of a half cell and electrode gel 103 can be considered to be the electrolyte portion of a half cell. In conventional terms of art, the combination of electrode and electrolyte and ECG electrode is typically referred to as a half cell. For example, the combination of a conductive surface 404 and an electrolyte layer (e.g., electrode gel 103) forms a half cell. For convenient quick reference to a half cell structure, the term "electrode" (assigned reference designator "109") is used interchangeably with "half cell" herein. It is understood that in typical embodiments, electrode 109 comprises conductive surface 404 and electrode gel 103.

Typically, electrodes make use of a circular or square conductive surface. Increasing the ratio of the perimeter of the surface to the area of the surface affects current density distribution and defibrillation recovery.

For convenience, we define the term "annulus" herein and throughout as the region between two simple curves. A simple curve is a closed curve that does not cross itself. Under this definition, an annulus can include substantially square shapes, substantially rectangular shapes, substantially circular shapes, substantially oval shapes, as well as substantially rectangular shapes with rounded corners. Further we include in the definition of annulus, the case of a substantially "U" shaped surface as described by a single closed curve.

One exemplary electrode gel 103 suitable for such use on a body worn monitor is type LT00063 hydrogel supplied by Tyco Healthcare of Prague, Czech Republic. Typically, a conductive surface 404 creates the electrode portion of the half-cell. By increasing the ratio of perimeter to area of the circular electrode portion of the half cell, the signal to noise ratio of the input ECG signal can be increased.

As depicted herein on the exemplary circuit layout, two batteries 304 can be connected in series, with one polarity being made available at connection pad 407 from battery connection 402, battery connection 401 creating the series connection between the two batteries, and connection pad 410, from battery connection 403, providing the second polarity of the series connected batteries. Note that in some embodiments, a single battery alternatively may be used in lieu of the exemplary arrangement or two batteries can be also wired in parallel, depending on the voltage requirements of a particular communications and computation module 102.

Connection pads 408 and 409 electrically couple the signals from electrode gels 103 (not shown in FIGS. 4A-4D) via conductive surface 404 and resistive traces 412 to electrical plug 302 (not shown in FIGS. 4A-4D). Electrode contact pad 405 can be connected via resistive trace 413 to connection pad 411 to provide a direct-connected reference electrode (not shown in FIGS. 4A-4D). Traces 412 extending between conductive surface 404 and connection pads 408 and 409 and trace 413 extending between conductive surface 405 and connection pad 411 can be made from resistive materials including resistive metals, carbon, silver ink, powders, paints, or other material of determinable electrical resistance.

Resistive traces on flexible circuit board layer 101 replace the bulky power resistors needed by prior art monitors, having electrodes or sensors connected by wires or leads. These resistive traces should survive multiple defibrillation cycles such that body worn monitor 100 remains functional even after one or more attempts to re-start a patient's heart. In order to survive defibrillation, the resistive traces should dissipate that portion of the potentially damaging defibrillation energy that is coupled into the monitor. This fractional portion of the defibrillation energy typically enters body worn monitor 100 from electrodes 109, FIG. 1D (electrodes 109 including conductive surface 404 and electrode gel 103).

It is desirable that the resistances of the protective resistive traces be in a range between about 1 kilo ohm to about 10 kilo ohms. Below 1 kilo ohm, depending on the resistive material used, it can be more likely that the resistance of the resistive traces 412 and 413 will increase with each successive defibrillation pulse. Above 10 kilo ohms, a high resistance impairs the signal to noise ratio, specifically due to thermal noise, which has a mean square value of $4*k*T*R*BW$, where "k" is Boltzmann's constant, "T" is temperature measured in degrees Kelvin, "R" is resistance in ohms, and "BW" is bandwidth, in Hz, which becomes significant relative to the EC-13 requirement that the noise referred to input be less than 30 μV peak-to-valley.

Power dissipation in the herein described traces can be calculated by $E^2/R$, in which E refers to the potential across the trace and R is the resistance of the trace. R can be calculated by $\rho*L/A$, where $\rho$ is the resistivity of the material used to form the trace, L is the length of the trace, and A is the cross-sectional area of the trace.

In developing resistive traces for use on a flexible printed circuit layer 101, typically formed on a MYLAR® substrate 406, such as shown in FIG. 4A, various materials were tested. Silver, including silver inks, while useable, was found to be less desirable, because it was difficult to achieve sufficiently thin silver traces on MYLAR® to achieve high enough resistances. Carbon, including carbon pastes and carbon inks, was also tried and found to be suitable. In order to use carbon however, several additional problems had to be solved. At 1 kilo ohm, the power dissipated by the resistors caused them to degrade across multiple defibrillation cycles. The solution was to make carbon traces in the range of about 8 to 10 kilo ohms. 10 kilo ohm resistances proved to be a good compromise between noise levels, power dissipation by the resistors, and manufacturing tolerances for depositing carbon ink on a MYLAR® substrate to dissipate the power from multiple defibrillation cycles. To achieve the desired resistance of about 10 kilo ohms (interchangeably represented herein as "10 k" or "10 kΩ"), for a given resistivity of the carbon paste, and given trace width and thickness (height), the length of the trace is then defined. In some cases, such as for traces 412, the length needed for a trace run, as between conductive surface 404 and connection point 409, might be longer than the length defined for a particular trace resistance (typically 10 k). In this case, traces can be extended by lengths of silver conductive traces. There can be a short overlay distance, on the order of 5 to 10 mm, in which a silver trace overlaps the carbon trace to provide a more robust connection between the resistive and conductive portions of the traces. Where overlap is used, the overall length of the resistive portion can be adjusted slightly to maintain the desired overall resistance.

Another problem associated with carbon traces was arcing at the interface between the carbon and conductive traces. Arcing was particularly problematic at the abrupt connection between the carbon trace and conductive surface 404. Arcing was also observed to occur between the end section of the carbon trace and conductive surface 404. (Electrode gels 103 create the conductive path to the patient through conductive surface 404 and a layer of conductive gel.)

Figure 4B:
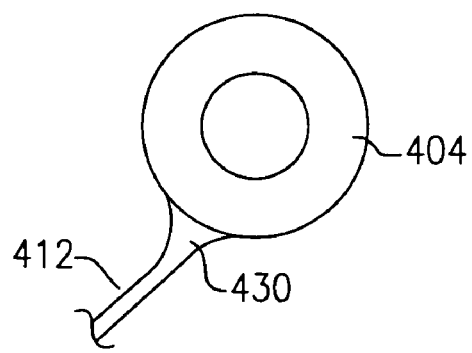
FIG. 4B shows a partial enlarged view of a portion of the flexible circuit board of FIG. 4A, further showing an exemplary resistive trace having a fillet.

According to one solution to the above noted arcing problem, as shown in FIG. 4B, a rounded (fillet) section 430 of carbon trace can be added at the interface to conductive surface 404. A fillet or "tear drop" shape causes the carbon trace to become gradually wider as it connects to conductive surface 404 and relieves the electrical potential stress at the interface.

Figure 4C:
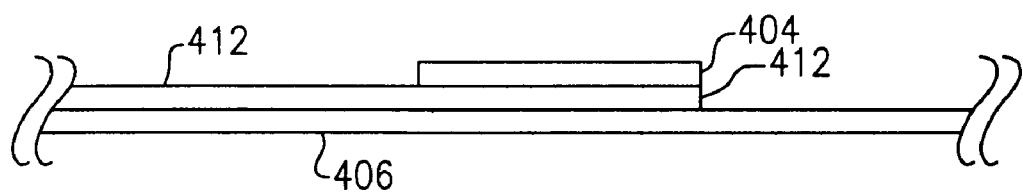
FIG. 4C shows a partial side elevated view of a portion of the flexible circuit board of FIG. 4A, further showing an exemplary conductive surface overlaying a resistive material.

An alternative solution to the arcing problem is shown in FIG. 4C, wherein carbon can be laid down beyond the trace (412) to include a pattern of conductive surface 404 formed from carbon. A carbon annulus pattern can be deposited before the conductive surface 404 is deposited. Conductive surface 404 can then be deposited as an overlay over the earlier formed carbon annulus shape. Finally, conductive gel 103 can be attached to the conductive surface layer (the carbon layer residing between conductive surface 404 and the MYLAR® substrate used as flexible circuit board 101). Both of the aforementioned arcing solutions can be used together. It should also be noted that conductive surface 404 can be formed from suitable materials other than silver, including, for example, materials such as silver chloride.

Arcing can also occur between the resistive traces and other (typically silver) conductive traces on the flexible circuit board 101. Trace to trace arcing can be suppressed by allowing sufficient spacing between the traces. Generally a minimum spacing of about 3 mm/kV, as required by ASNI/AAMI DF80:2003 57.10 BB, has been found to be sufficient to prevent trace to trace arcing from a defibrillation event. Closer trace spacing, as close as 0.01 mm/kV, can be employed successfully by first applying an insulating dielectric layer, similar to a conformal coating, over the surface of flexible circuit board 101 that covers most of the substrate and traces. The insulating dielectric layer can be prevented from forming or adhering to conductive surface 404, such as by use of a mask during application of the insulating layer.

Figure 4D:
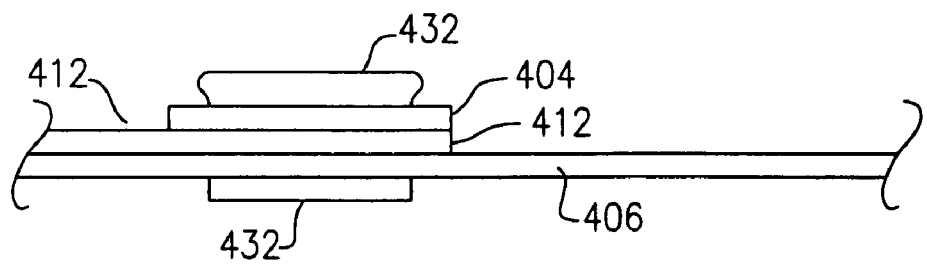
FIG. 4D shows a partial side elevational view of the circuit board of FIG. 4A, further showing an exemplary conductive surface having a snap receptacle.

In an alternate embodiment, as depicted in FIG. 4D, a snap device can be added to conductive surface 404 to accept a manufacture snap-on electrode (not shown), such as, for example, the ConMed Cleartrace line of ECG electrodes including the model 1700 Cleartrace electrode manufactured by the ConMed Corp. of Utica, N.Y. or similar type electrodes made by the 3M Corp. of St. Paul, Minn. When designed to accept a snap-on electrode, the conductive surface 404 is typically smaller than in the previous embodiment. A receptacle snap 432 for receiving the commercial snap-on electrode can be inserted by any suitable method, such as by press fitting or other fastening method, into conductive surface 404, typically also penetrating through substrate 406. In this embodiment, arcing can be similarly suppressed in this embodiment by adding a fillet to the carbon-conductive surface interface and/or deposing a conductive surface 404 over a carbon layer as previously described.

Example: Resistive traces and an annulus were tested on a substrate formed from CT3 heat stabilized treated polyester (75 microns thick), such as manufactured by the MacDermid Autotype Corp. of Schaumburg, Ill. Resistive traces were silk screened onto the substrate using 7102 carbon paste conductor from the DuPont Corporation of Wilmington, Del. The carbon paste conductor was deposited through a 43T silk screen mesh. The substrate containing the paste deposit was then cured inside a fan assisted air circulated oven at 120° C. for a period of 5 minutes. The traces formed were about 55 mm long and 2 mm wide, having an overall thickness of about 7.5 microns. The initial measured resistance of each trace was about 14 kilo ohms. After each trace was subjected to 3 defibrillation cycles, the measured resistance increased to about 15 kilo ohms. Over a 3 mm length, the trace widens to about 5 mm, terminating into a carbon annulus with an outer diameter of about 20 mm and an inner diameter of about 10 mm. A silver layer of PF-410 silver ink from the Norcote Corp. of Eastleigh Hampshire, UK was then deposited over the carbon annulus, also to an overall thickness of about 7.5 microns. The deposition of the silver layer was via the silk screen printing method, in which a 90T silk screen mesh was used. The substrate containing the deposited silver ink was then cured inside a fan assisted air circulated oven at 120° C. for a period of 15 minutes. A third dielectric insulating layer comprising SD2460, components A & B (dielectric and hardener), manufactured by Lackwerke Peters GmbH+Co KG of Kempen, Germany, and having a thickness of approximately 13 microns was then deposited over the traces and substrate, but not over the annulus. (The electrodes were formed by attaching a conductive gel to the annulus. The conductive gel used was LT00063 hydrogel from Tyco Healthcare of Prague, Czech Republic.) Again, the silk screen printing process was used to deposit the dielectric layer through a 90T screen mesh. The substrate was placed again into a fan assisted air circulated oven at 120° C. for a period of 30 minutes.

Example: Silver traces for use as conductive (not resistive) traces on a body worn monitor circuit substrate were formed from a silver paste that was silk screened onto a MYLAR® substrate. 45 mm long traces had a measured resistance in a range of 3.5 to 6 ohms, 75 mm traces had a measured resistance in a range of 6.5 to 13 ohms, and 105 mm traces had a measured resistance in a range of 10 to 16 ohms. The deposition of the silver layer was performed via the silk screen printing method in which a 90T silk screen mesh was used. The substrate containing the deposited silver ink was then cured inside a fan assisted air circulated oven at 120° C. for a period of 15 minutes.

Figure 15:
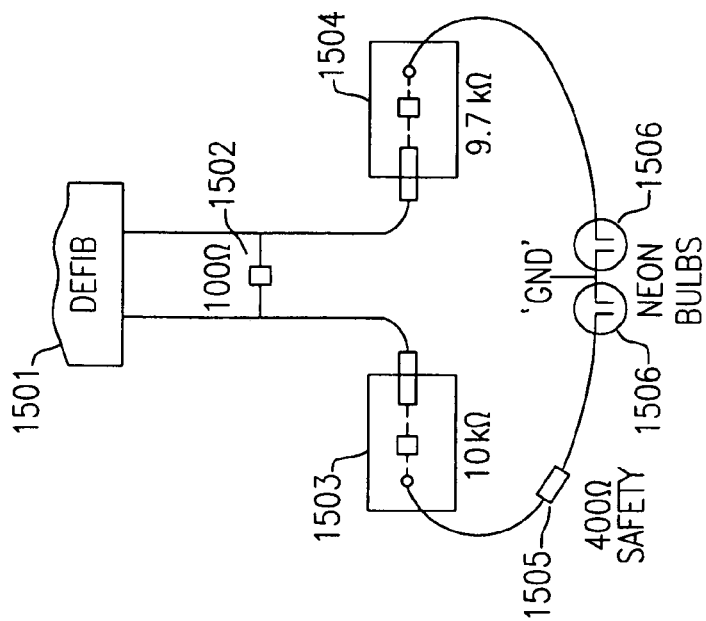
FIG. 15 shows a block diagram of a setup for simulating the effect of patient defibrillation on resistive traces.

FIG. 15 diagrammatically depicts an exemplary test setup used to simulate the effect of a patient defibrillation on resistive traces. Defibrillator 1501 was used to apply multiple defibrillation shocks of 360 Joules each to the 100 ohm resistor 1502. The 100 ohm resistor according to this setup simulated a patient's body. Note that most of the defibrillation energy goes into the patient's body by design, to restart the patient's heart. Resistive traces 1503 and 1504 were wired across resistor 1502, also as shown in FIG. 15, in order to simulate the electrical circuit that would be formed between the resistive traces in a body worn monitor situated on a patient undergoing defibrillation. Neon bulbs 1506 were used as part of the protection circuitry that can be used with resistive traces in a body worn monitor. 400 ohm safety resistor 1505 was present as a precaution to limit short circuit current in the event of a test setup failure. Both the 100 ohm resistor (simulating human skin resistance) and the 400 ohm safety resistor were used in accordance with medical specification AAMI EC-13. Following 3 defibrillation shocks of 360 Joules each, the measured resistance of the 10 k carbon track changed from 10 k to 11 k following the first shock, to 13.1 k following the second shock, and to 13.2 k following the third shock. The measured resistance of the 9.7 k trace changed from 9.7 k to 11.6 k following the first shock, to 13.0 k following the second shock, and finally to 13.2 k, following the third shock. In a subsequent related test, the 100 ohm resistor was replaced by a closer simulation in the form of a fresh (dead) chicken. The setup otherwise remained the same as shown in FIG. 15. In this case, the resistance as measured on each of the test resistive traces changed from 10.7 k to 10.25 k, and from 8.5 k to 9.4 k, following multiple defibrillations. During testing, it was also noted that the change in measured resistance of the resistive traces was generally consistent. It was also noted that as a given resistive trace was increased, the (delta R {caused by defibrillation}/R {net trace resistance}) can be minimized.

Figure 16A:
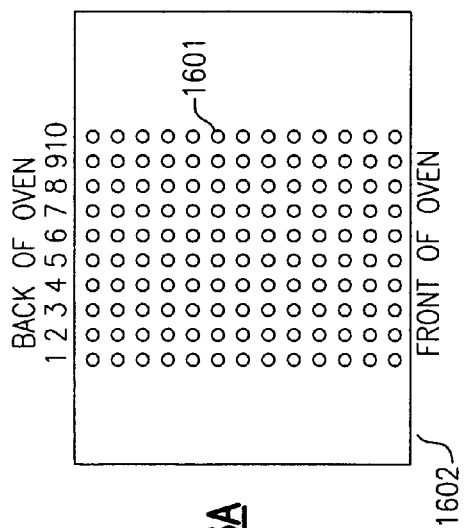
FIG. 16A symbolically shows resistive dots silk screened on a tray.
Figure 16B:
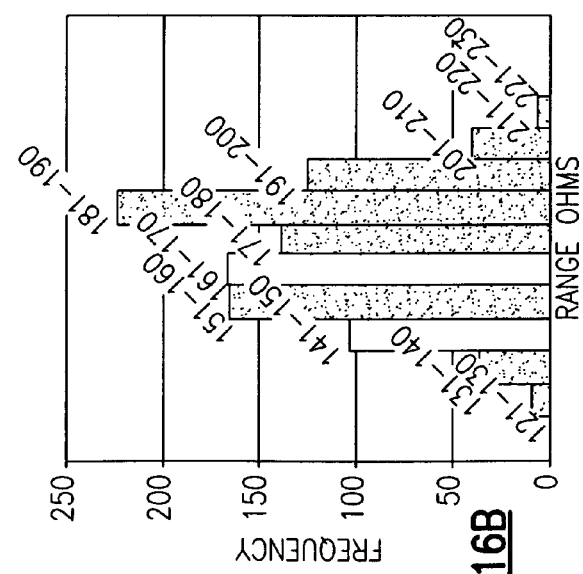
FIG. 16B shows a histogram of an exemplary resistive distribution of baked resistive dots.

The screen printing technique for laying down resistive traces was further investigated by printing a plurality of small carbon resistive dots 1601 of about 20 mm in diameter using a 7102 carbon ink applied by a screen printer (not shown). The carbon dots 1601 were laid out on a tray 1602 as shown in FIG. 16A, for baking in an oven. A manually operated squeegee (not shown) was used to apply the resistive dots 1601 to the tray 1602 through a mask (not shown). It was determined that control of thickness during application was one important factor for controlling the distribution of resistance. It was noted that during manual application, the variation of resistance depended upon the distance between the plurality of dots 1601 and the person applying the resistive paste, and that the pressure applied using the squeegee could also affect the final resistance by a factor of two. It was further noted that "even" heating across the tray 1602 was advantageous during oven drying, although this factor was found to have less effect on the final dot resistance distribution. A resistance distribution of the baked and measured dots 1601 is shown in the histogram of FIG. 16B. This testing indicated that production traces laid down on a substrate, such as MYLAR®, for use in a body worn monitor should preferably be printed using a semi-automatic screen print process, such as by a screen printing mechanical roller process. A digital multimeter ("DMM") with probes placed at each edge of a dot 1601 was used to measure the resistance from one edge of the dot to the other. It was found that uniform application of ink was important to keeping a tight distribution of resistance, with even heating having a smaller influence on the distribution of the resistance of the test dots. Since a trace with too low a resistance has a greater ΔR/R, and higher probability of failing and very high resistance traces result in worse S/N ratio, it is important to have a reasonably tight tolerance on the trace resistance.

Figure 5:
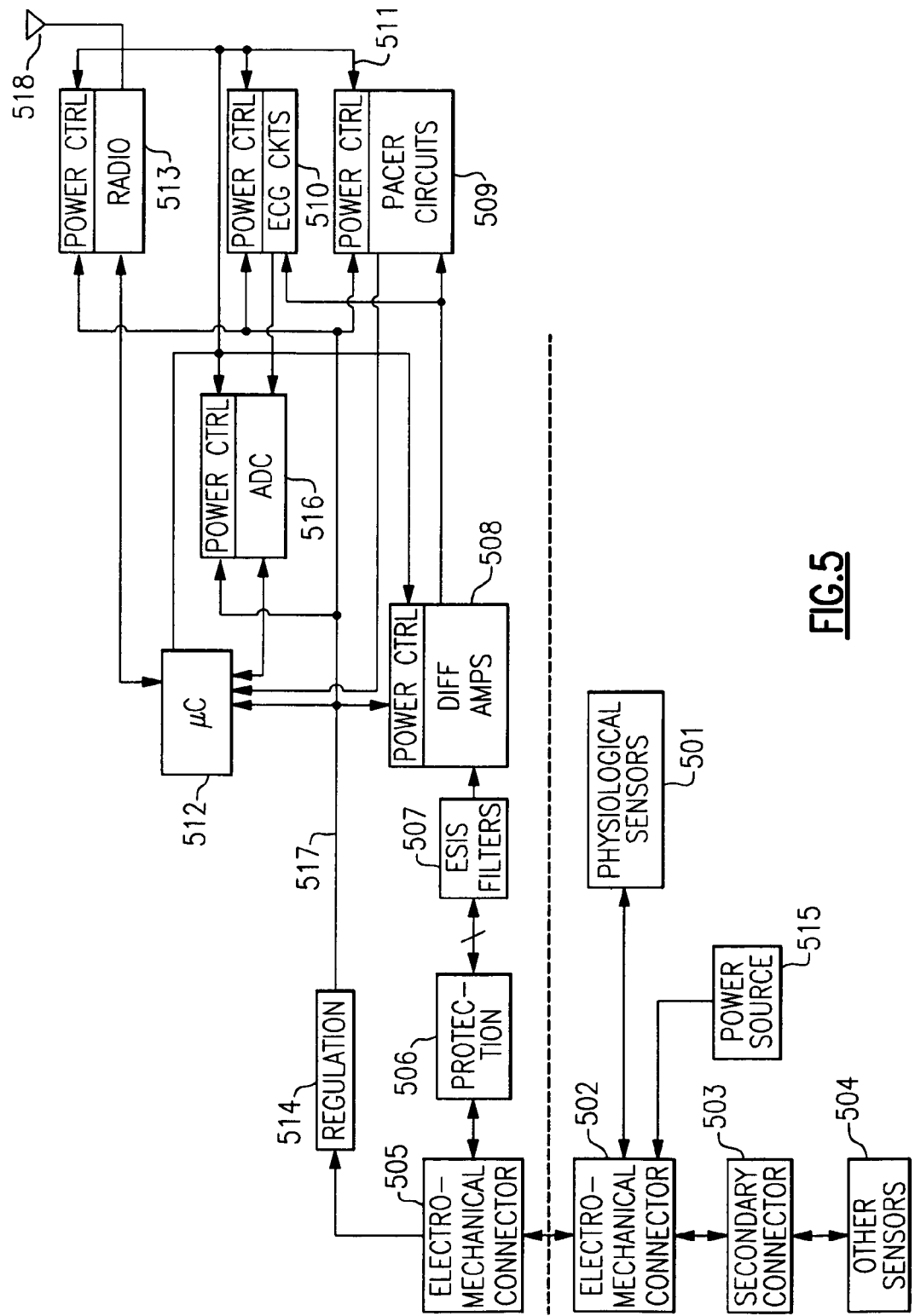
FIG. 5 shows a block diagram of one embodiment of a body worn physiological monitor having a power source in a disposable unit.

FIG. 5 shows a block diagram representative of one embodiment of the body worn physiological monitor 100. Physiological sensors 501 (such as electrodes 109 in FIG. 1D) can be electrically coupled to electromechanical connector 502 (as by the resistive traces 412 shown in FIG. 4). Connector 502 serves to electrically couple communications and computation module 102 to a disposable electrode module 110 (FIG. 2). Secondary connector 503 can also electrically couple one or more additional sensors, which can be situated both on and off of disposable electrode module 110, to electromechanical connector 502 for electrical coupling along with physiological sensor signals 501 to communications and computation module 102 (shown in FIG. 1) via electromechanical connector 505. Signals received by the communications and computation module 102 can be electrically coupled into communications and computation module 102 via electronic protection circuits 506 and/or filters, such as ESIS filters 507.

Signals can be limited or clipped in amplitude, as needed, by protection circuit 506, and filtered by filter 507. One or more analog amplifiers 508 can be used to amplify the amplitude limited and filtered signals. In the exemplary body worn ECG monitor, amplifiers 508 can advantageously be differential amplifiers to amplify the difference signal (e.g. the ECG "vector") between two ECG electrodes. The electrical output of amplifiers 508 can be electrically coupled to both PACER circuits 509 and ECG circuits 510. PACER circuits 509 are described further below. ECG circuits 510 perform several functions, including "trace restore", low pass filtering (anti-aliasing), high pass filtering, and amplification (gain). Low pass filtering filters signals according to the Nyquist criterion to avoid aliasing later when the signals are digitized by analog to digital converter (ADC) 516. The high pass filter causes the input to be AC coupled from a roll off frequency of about 0.05 Hz, as specified by industry ECG standards. Gain is required to cause the small pre-amplified potentials from physiological sensors (such as electrodes 109) to more closely match the available dynamic range of the digitizing ADC 516. Note that ADC 516 can be a dedicated ADC chip or can be included in a microcomputer integrated circuit, such as a microcomputer serving as microprocessor 512.

A microprocessor, such as microprocessor 512, is defined herein as synonymous and interchangeable with the terms "microcomputer", "microcontroller", and "microprocessor". Such microprocessors are also interchangeably represented herein as "μP" or "μC". Further, any microprocessor disclosed herein can be replaced by any integrated device that can perform the function of a microprocessor, such as, but not limited to, a field programmable gate array ("FPGA") programmed to perform the functions of a microprocessor.

Typically, one or more differential amplifiers can be dedicated to particular difference voltages associated with physiological sensors 501 or 504, but it should be noted that one or more amplifiers 508 can also be multiplexed by techniques as known in the art, to serve multiple physiological sensors using a lesser number of amplifiers. Similarly, one or more ADCs 516 can serve two or more signals from physiological sensors 501 or 504 using techniques such as multiplexing in time that is digitizing one physiological sensor difference signal at a time sending a digital result to a next stage one after the other. ECG circuits 510 and PACER circuits 509 are referred to in the plural, since there can be individual circuits for each measured physiological signal, such as for each measured ECG vector.

Electrical power from power source 515 can be regulated by regulator 514 and distributed as regulated voltage 517 to most function blocks (as represented herein by the label "POWER"), such as including the function block radio 513 which is electrically coupled to antenna 518. Each of these function blocks also has a control ("CTRL") input 511 from microprocessor 512, allowing these circuits to be disabled, when not needed, in order to save battery power. When viewed over time, most of the ECG waveform does not contain useful information since there is significant "dead time" between heart beats. Therefore, for example, from the end of a "T wave" at the end of one heart beat to the beginning of a "P wave" at the beginning of the next heart beat, circuits can be powered down (in a device "sleep mode") to save on the order of 60% of the energy stored in the power source that would have otherwise been used during this dead time.

Figure 17:
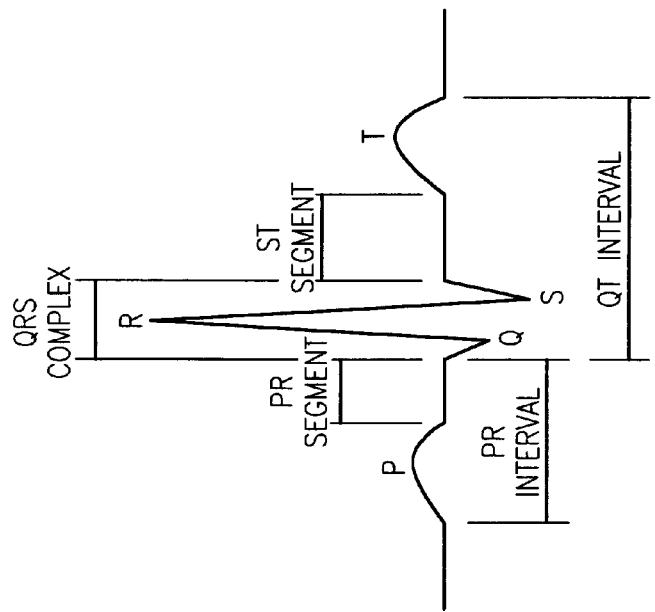
FIG. 17 shows an exemplary ECG waveform.

FIG. 17 shows an exemplary ECG waveform. In brief, the P wave can be related to the electrical current causing atrial contraction. The QRS complex can be related to ventricular contraction of the left and right ventricles. The Q wave can be related to electrical current traveling through the intraventricular septum, while the R and S waves can be related to the ventricles contracting. The T-wave is due to the re-polarization of the ventricles. Usually, atrial re-polarization occurs atop the QRS complex, and being much smaller than the QRS complex, is not seen. The ST segment connects the QRS complex to the T-wave. Irregular or missing waves may be indicators of cardiac issues including: ischemic tissue, e.g. due to myocardial infarction, bundle branch block, atrial problems (specifically P-wave abnormalities), pericarditis, and electrolyte disturbance.

Figure 6:
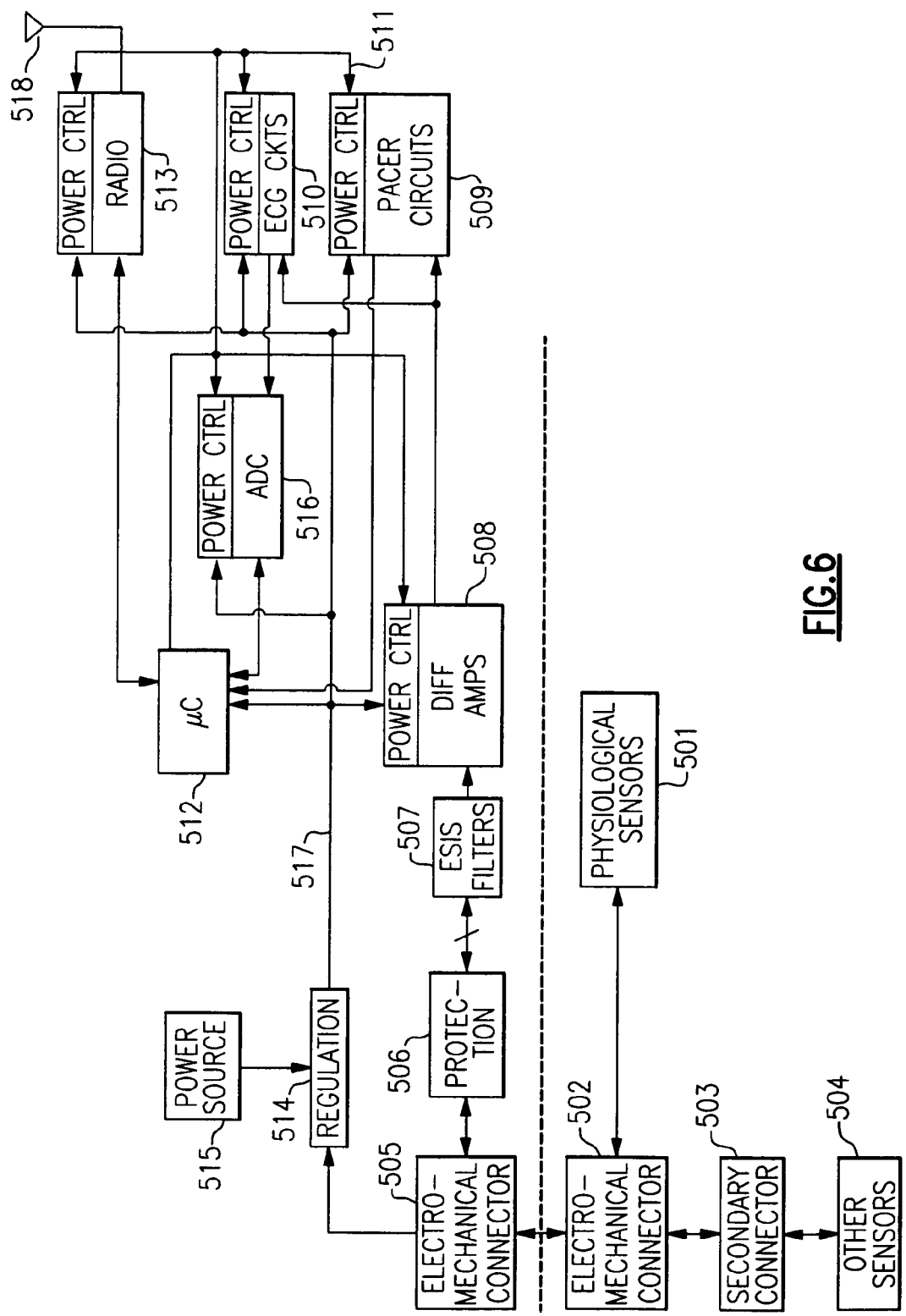
FIG. 6 shows a block diagram of one embodiment of a body worn physiological monitor having a power source in or connected to the computation and communication module.

Generally, power source 515 can include one or more "button" cells typically disposed on disposable electrode module 110; however, the block diagram of FIG. 6 shows an embodiment of a body worn physiological monitor 100 where power is supplied by a power source located on, or connected to communications and computation module 102 instead of residing within disposable electrode module 110.

Beyond power saving considerations, it can also be desirable in some embodiments of body worn physiological monitor 100 to put the microcontroller and/or other circuits, including particularly digital circuits, into a sleep mode during an ADC conversion cycle to minimize pickup of self generated electrical noise and to minimize power use. Preferably, the A/D circuit can acquire multiple samples and buffer the samples, before awakening the microprocessor, which then can batch-process the data. Buffering can be set to match the patient's heart rate, as there is no significant clinical benefit to analyzing every sample as it is taken.

Turning back to the input circuits, typically amplifiers 508 are differential or instrumentation amplifiers useful to selectively amplify desired difference signals between connector terminals (such as an ECG vector), while rejecting common mode signals (such as interfering signals that appear simultaneously on both connector terminals). Beyond using a differential amplifier, other techniques can be advantageously used to further reduce common mode pickup (CMR) and thus to improve the common mode rejection ratio (CMRR) of the input amplifier stages of body worn physiological monitor 100. CMR is of particular concern with regard to body worn physiological monitor 100 because of the proliferation of potentially interfering electromagnetic fields, such as from 50 Hz or 60 Hz AC power line distribution throughout a hospital. For example, many fluorescent ceiling lamp fixtures generate strong 60 Hz alternating current (AC) electromagnetic fields that can appear as common mode signals on physiological sensors 501, such as ECG electrodes 109.

Figure 7A:
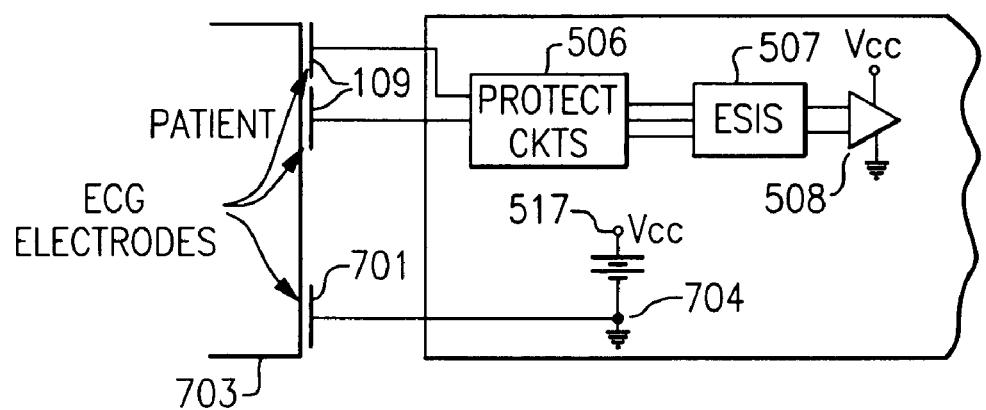
FIG. 7A shows a schematic diagram of a direct connected reference electrode used in conjunction with a body worn physiological monitor.

FIG. 7A shows one embodiment in which body worn physiological sensor 501 comprises a plurality of ECG electrodes 109 and 701. Two electrodes 109 generate an ECG difference potential for patient 703. A third electrode, reference electrode 701 can be electrically coupled to electronics common 704 (or other potential level) and can be used to improve CMR. In this embodiment, the electronics common 704 (shown as the negative terminal of the battery in FIG. 7A) can be directly tied to the patient in the vicinity of electrodes 109. Thus, the electronics common of the electronic circuits in communications and computation module 102 can be made to more closely follow any change in potential in the vicinity of electrodes 109. Reference electrode 701 can be particularly helpful to ensure that inputs 109 remain within a reasonably narrow common mode range, such as by reducing a 60 Hz potential that would otherwise appear to move the electronics common 704 at 60 Hz with respect to electrodes 109.

Figure 7B:
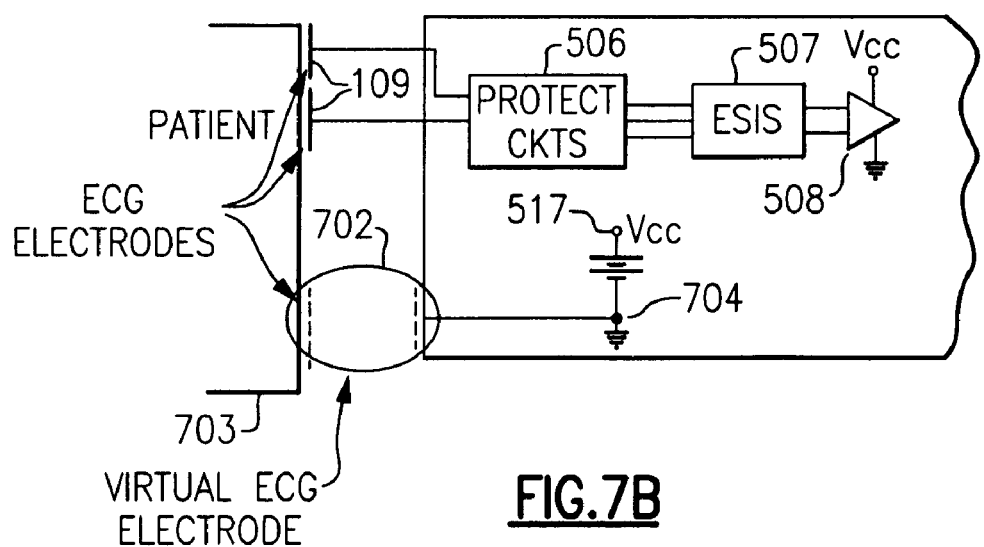
FIG. 7B shows a schematic diagram of a virtual reference electrode as used in conjunction with a body worn physiological monitor.

In another embodiment as shown in FIG. 7B, virtual electrode 702 performs a similar function as previously described with regard to reference electrode 701. In this embodiment, instead of creating a DC-coupled reference electrode, electrode 701 is replaced by the capacitive coupling between flexible printed circuit layer 101 and the patient 703, resulting in a virtual electrode 702 with an AC coupled common. Such AC coupling increases with decreased distance between flexible printed circuit layer 101 and the patient and can advantageously reduce 60 Hz common mode signals (AC signals).

Figure 8:
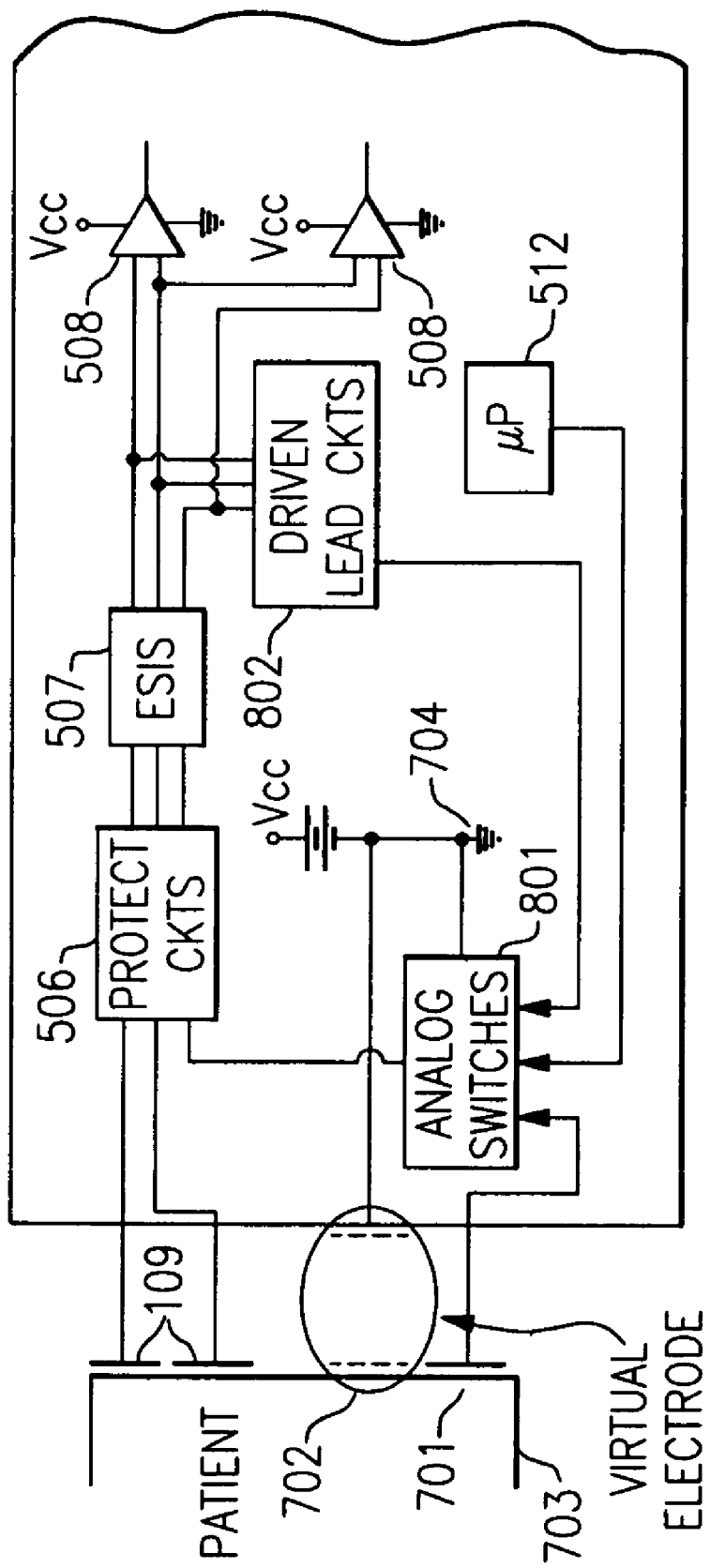
FIG. 8 shows a schematic diagram depicting one embodiment of an analog switching arrangement provided on a body worn physiological monitor to select a reference electrode configuration.
Figure 8A:
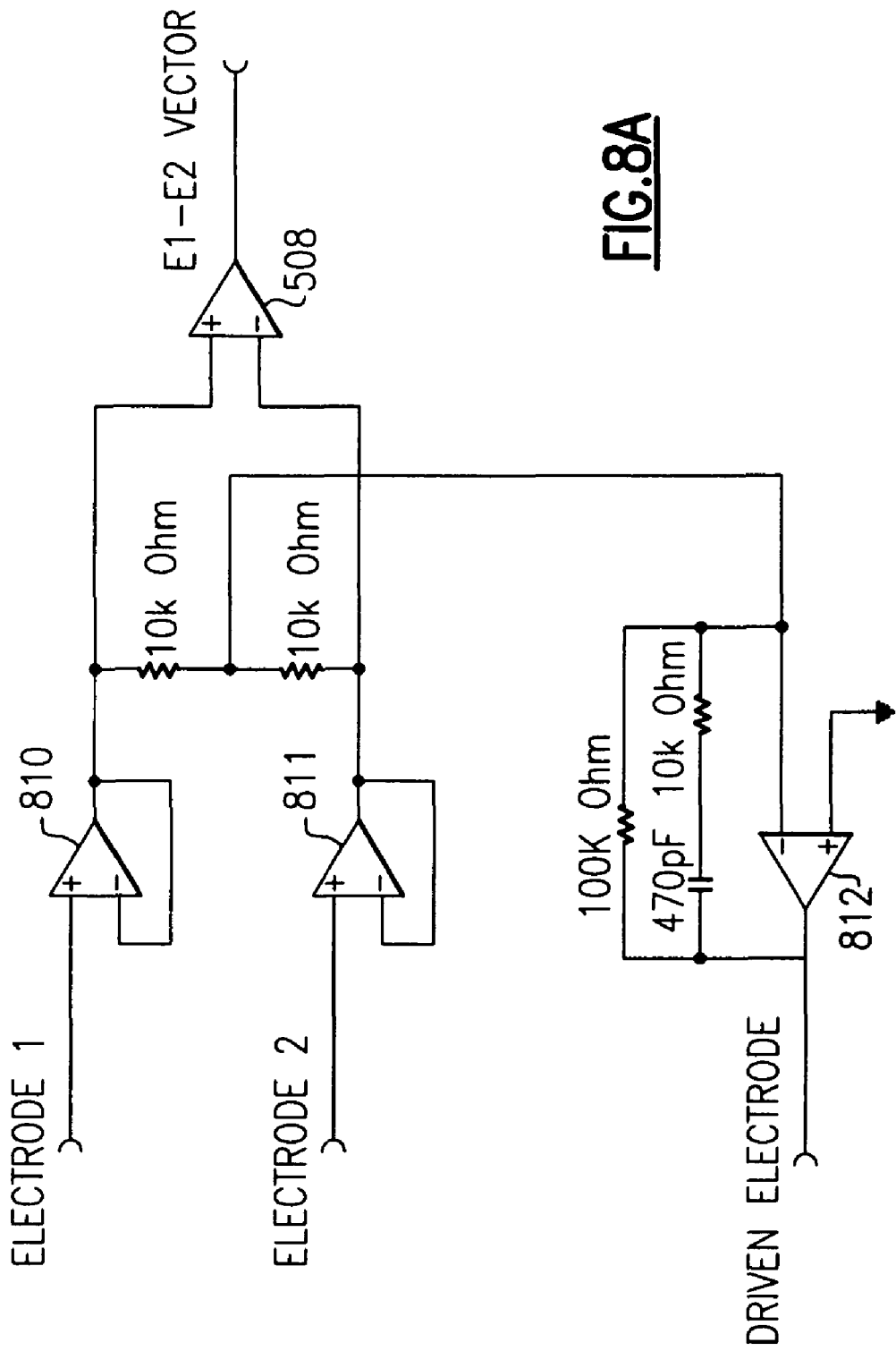
FIG. 8A shows an exemplary driven lead circuit topology for use with electrodes of a body worn physiological monitor.

In yet another version of a directly connected electrode 701, as shown in FIG. 8A, electrode 701 can be actively driven by an electrical output from communications and computation module 102. Typically, an operational amplifier (OpAmp) or other type of amplifier can be used to create a "driven lead". Driven lead circuits can be used to further improve CMR over passive electrodes 701 as shown in FIG. 7A. An exemplary circuit suitable for use to drive an electrode 701 is shown in FIG. 8A. Amplifiers (OpAmps) 810 and 811 buffer the high impedance signals from electrode 1 and 2 (exemplary electrodes 109). Difference amplifier 508 conveys the difference signal (such as an ECG vector) as previously described. The two 10 kilo ohm resistors provide an average of the common mode signals appearing simultaneously at the inputs of buffer amplifiers 810 and 811. The inverting low pass filter built around OpAmp 812 inverts the averaged common mode pickup signal (at electrodes 1 and 2) and applies that signal out of phase (180 degree phase shifted) to a directly connected driven electrode (such as electrode 701). By applying the average common mode signal to the driven electrode, amplifier 812 effectively suppresses common mode signals at electrodes 1 and 2 within the effective bandwidth of the negative feedback loop by active noise cancellation. In theory, a virtual electrode 702 could be similarly driven, but the voltage requirements to drive a capacitively coupled common electrode are high enough to make a "driven virtual electrode" a less practical option. Thus, it can be seen that a reference electrode can be a passive connection or an actively driven connection.

It can also be desirable to have more than one CMR technique available. For example, in a low noise environment, a lower power reference electrode might be used for CMR. Then if the noise increases to a level where the reference electrode provides insufficient CMR, the body worn monitor can switch to a driven lead more suitable for CMR in a high noise environment. In this embodiment, a particular CMR configuration can be selected by electronic switching. FIG. 8 shows one such exemplary switching block represented as reference electrode switch 801. Microprocessor (µP) 512 can control reference electrode switch 801 to select direct connected electrode 701, virtual electrode 702, or directly connected electrode 701 additionally driven by a driven lead circuit 802. It should also be noted that in the embodiment of FIG. 8, when virtual electrode 702 provides sufficient CMR, electrode 701 can be used as a third electrode, thus allowing body worn monitor 100 to simultaneously measure two different heart vectors.

Figure 9:
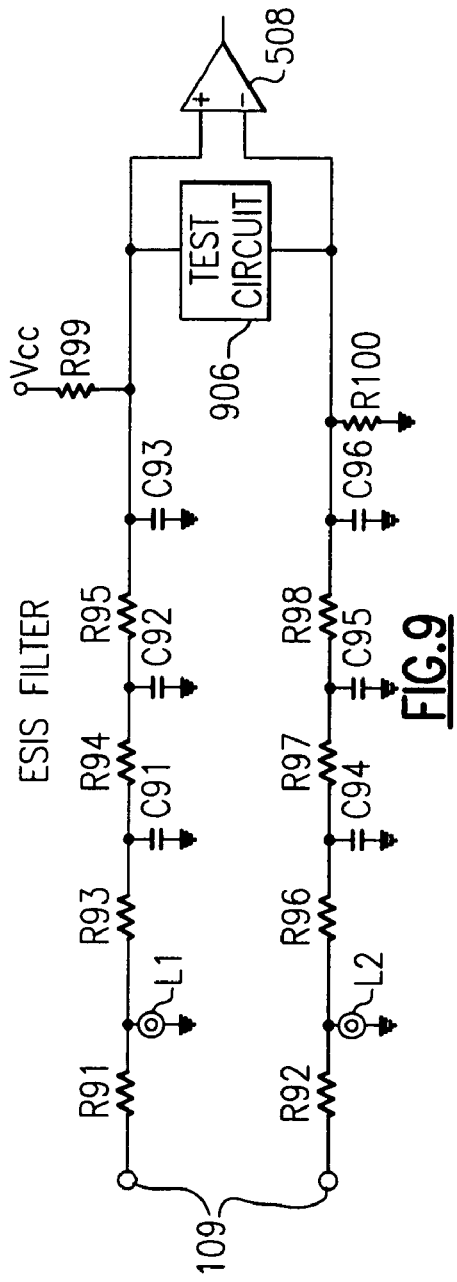
FIG. 9 shows an exemplary ESIS filter circuit topology with circuit protection.

FIG. 9 shows one embodiment of an exemplary defibrillation protection circuit (506) and ESIS filter 507. As shown in FIG. 9, electrodes 109 can be connected via input resistors R91 and R92. Gas discharge tubes, such as neon bulbs L1 and L2, can be used for over voltage protection by firing at a designed voltage to prevent large potentials from appearing at the input leads to amplifier 508. The gas discharge tubes can be disposed on either disposable electrode module 110 or on the communication and computation module 102. Defibrillation protection resistors R91 and R92 can further reside in disposable electrode module 110, such as in the form of the resistance of traces 412.

ESIS filters 507 can be used to satisfy AAMI standard EC13 on Electrosurgical Interference Suppression (ESIS). Standard EC13 addresses the ability of an ECG monitor to display and process ECG signals in a satisfactory manner while connected to a patient on whom an electrosurgical device is being used. Without such suppression, the high RF output of an electrosurgical device can render ECG monitoring impossible and or render the monitor unusable. Resistors R93 to R98 and capacitors C91 to C96 form cascaded low pass filter sections (e.g. R93-C1). Three cascaded single pole filters are shown on each input leg of amplifier 508 as an example; more or less stages can also be used. It is also not necessary for each section of the cascaded filter to have identical values or roll off points in the frequency domain to create a specific response, e.g., Bessel, Chebychev, or other filter response known to those skilled in the art. Also, ESIS filters are not limited to cascaded single pole filters and can take other forms as known in the art.

Test circuit 906 can provide a relatively sharp transient signal for testing the PACER circuit described below as part of a body worn monitor 100 "power on self test". Resistors R99 and R100 can pull the output of the differential amplifier 508 allowing the microcontroller (512) to detect which electrode, if any, has detached, much as a "lead failed" detection is accomplished by ECG monitors having leads. Body worn monitor 100 does not use leads, but it is still possible for one or both of the physiological sensors to move free of a patient's body. Such disconnects can occur in situations in which body worn monitor 100 partially moves away from the body to which it is non-permanently affixed. The input impedance at one or both of the electrodes 109 changes in a sensor off (sensor disconnect) event. When a patient is attached, amplifier 508 typically has an output voltage of near zero volts. However, if one of the electrodes 109 comes off, resistors R99 or R100 cause the output of amplifier 508 to move to a most positive output ("positive rail") or to a most negative output ("negative rail"). Note that the negative rail can be a small voltage near zero, in the case of single supply circuit operation, and that both inputs could be pulled to the same rail. Lead-fail detection can also be analyzed to determine when the device is attached to the patient and then to automatically enter full operational mode. Such analysis can be done at a low frequency.

The ESIS filter 507 also can cause a stretching in the time domain of a pacer pulse so that the event is recorded by at least one sample, even though the pacer pulse itself is of small duration compared to the ADC sample rate and the pacer pulse is likely to occur between samples.

Figure 10:
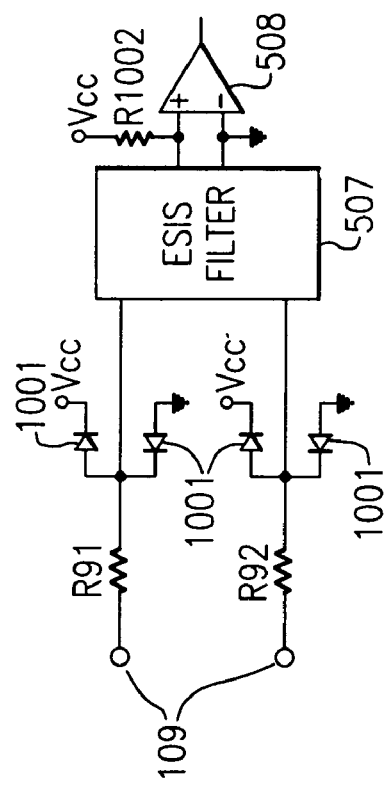
FIG. 10 shows an alternative circuit protection to that depicted in FIG. 9.

FIG. 10 shows an alternative circuit to accomplish over voltage protection, such as is required during defibrillation. In FIG. 10, diodes 1001 prevent the electrode potentials from going much more than one diode voltage drop above Vcc or below ground and resistors R91 and R92 limit current. Using circuit protection, such as gas discharge tubes L1 and L2 (FIG. 9) and/or diodes 1001 (FIG. 10) combined with resistances R91 and R92, typically in the form of resistive traces 412, a body worn device can survive multiple defibrillation cycles of at least 360 joules.

PACER circuit 509 detects pacemaker pulses. One reason to detect a pacemaker is to prevent the ECG circuitry from inadvertently registering the regular pulses from a pacemaker as an actual heart rhythm. Separation of a pacemaker signal from signals generated by the heart is important both to generate accurate ECG analysis results as well as to correctly detect the absence of an actual heart rhythm. For example, a pacemaker continues to function even where a human heart has completely failed.

A pacer event (pacemaker signal) is typically a narrow pulse typically less than 100 microseconds wide. Because of the capacitance between the pacer in a patient and an ECG circuit, an otherwise relatively square pacer pulse as administered at the patient's heart by a pacemaker, can appear to an ECG monitor as a pulse with a negative undershoot and an exponential return to zero that could inadvertently mimic a QRS signal. A pacer signal, however, can be recognized by an analog differentiator and alert microprocessor 512 to the presence of a pacer and to disregard the refractory period of the corresponding R-C recovery due to the pacer signal. The pacer detection circuit or PACER circuit can generate a microprocessor interrupt to inform the microprocessor that a pacer event occurred and to mark a corresponding physiological signal in time as related to a pacer event. PACER circuit 509 can also cause one or more pacer related circuits to automatically power down for power saving, where it is determined that a patient is not using a pacemaker.

Figure 11:
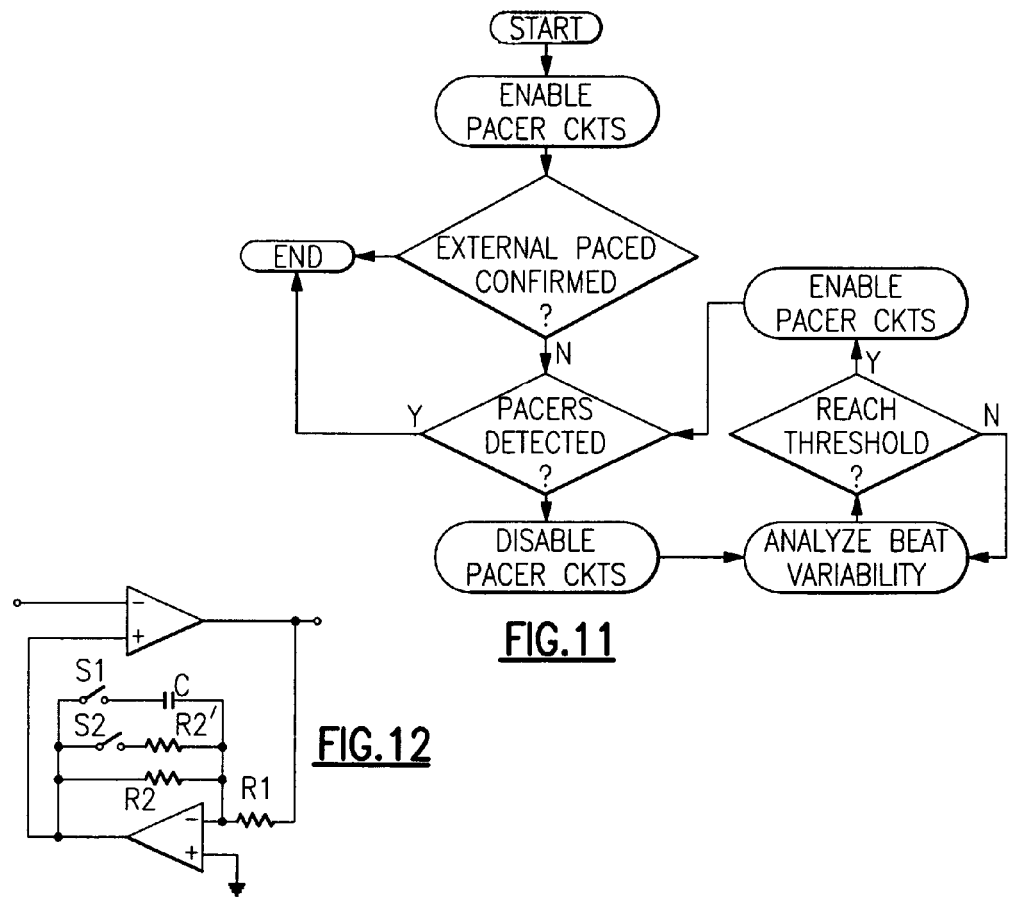
FIG. 11 shows a flow chart for an algorithm utilized by a body worn physiological monitor to detect whether a patient has a pace maker.

FIG. 11 shows an algorithm useful to determine if the pacer circuit should be enabled. A typical PACER detection circuit uses a significant percentage of the energy available from a power source such as batteries 204. If a PACER signal is not detected, such as at power up of body worn monitor 100, the pacer circuit can be automatically disabled allowing for a longer battery life. Since typical PACER circuits can use several amplifiers (OpAmps), they can consume up to one third of the analog power, therefore securing the PACER circuits when they are not needed (i.e. the patient does not have a pace maker) can cause a significant improvement in battery life. The algorithm also can also provide checks to determine if a demand type pace maker begins operation (which might be inactive at power up of body worn monitor 100) by analyzing beat variability. While it can be advantageous to have the body worn device automatically sense the presence of a pacemaker and to enable the PACER detection circuit, the choice as to whether to enable or disable the PACER circuit can also be done by externally configuring the body worn device. Such external configuration can be done through a hardwired communication connection cable or via communications and computation module 102, in which communications and computation module 102 is a two-way radio transceiver communication device capable of receiving a configuration command sent for a remote radio transceiver. The radio could be 802.11 compliant, but generally would use a lighter-weight (simpler) protocol that can be more energy efficient. A suitable lighter weight protocol could be proprietary, or standards-based, such as ZigBee or Bluetooth. A body worn physiological monitor 100 is particularly well suited for use in hospital environment as part of an integrated wireless monitoring network. The details of such monitoring networks are disclosed in U.S. patent application Ser. No. 11/031,736 entitled, "Personal Status Physiological Monitor System and Architecture and Related Monitoring Methods", which is incorporated by reference herein in its entirety.

Figure 12:
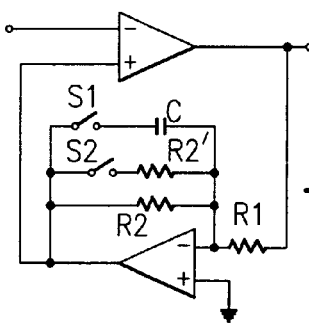
FIG. 12 shows a circuit topology of a high pass filter useful for baseline restoration.
Figure 13:
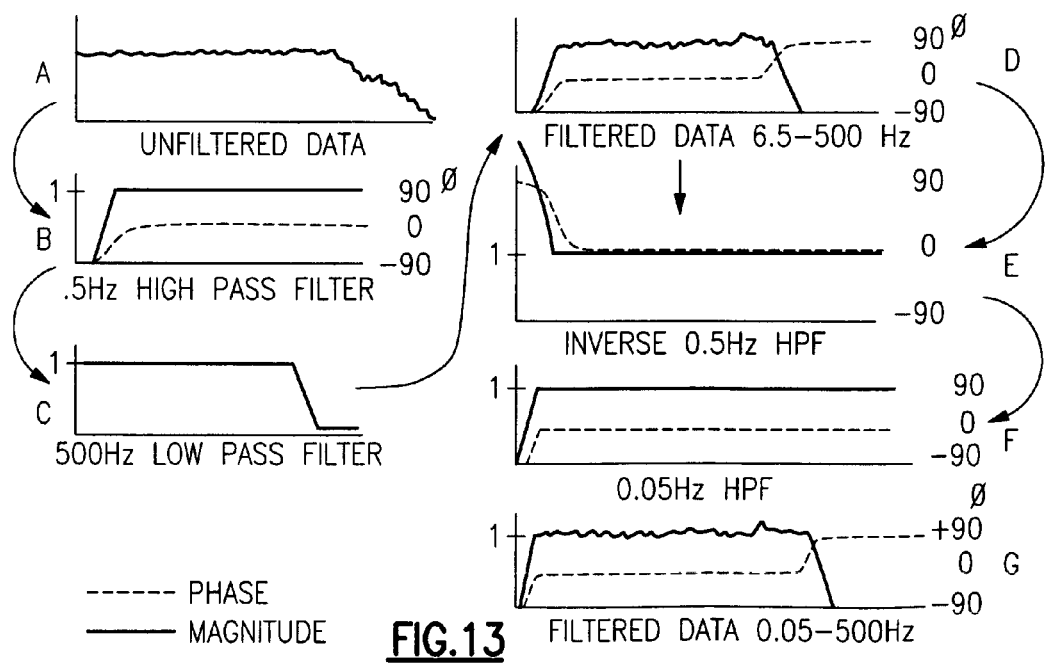
FIG. 13 shows seven graphs of amplitudes plotted versus frequency to illustrate exemplary operation of the circuit of FIG. 12.

FIG. 12 shows a high pass filter (HPF) suitable for use in ECG circuits block 510. An advantage of a 0.5 Hz HPF is faster recovery from DC offsets due to patient movement, defibrillation, electrocuatery, etc. However ST segment analysis is negatively impacted if HPF cutoff is greater than about 0.05 Hz. Thus, it is preferable to have the ability to change between a 0.5 and 0.05 Hz cutoff frequency. The high pass filter of FIG. 12 is implemented by a low pass filter configured as an inverting amplifier in a negative feedback circuit to give a net effective high pass transfer function from circuit input to output. The corner frequency of the composite filter can be adjusted by switching in resistor R2'. Alternatively, S1 can be switched at a periodic rate to place a duty cycle on C. Note that the frequency of switching of S1 should be fast with respect to the corner frequency of the anti-aliasing low pass filter. The graphs A-D of FIG. 13 further illustrate the performance of the exemplary filter of FIG. 12. These graphs show normalized amplitude on the vertical axis plotted against frequency on the horizontal axis. FIG. 13, graph A represents a raw input signal. FIG. 13, graphs B and C are Bode Plots representing the high and low-pass filter sections. After applying filter responses B & C to input Data A, filtered data D is the result. The HPF cutoff can be 0.5 Hz or some lower value depending on whether R2' is switching in or if C is duty cycled.

Another method to achieve this frequency change is to use digital filters implemented on Microprocessor 512 to reverse the effects of the 0.5 Hz HPF, then implement a digital HPF at a lower cutoff frequency, 0.05 Hz, for example. The response of the 0.5 Hz filter should be known to implement the inverse filter. This response can be measured using microprocessor 512 to trigger the test circuit 906 to create an impulse, H(s). The inverse filter is the [1-H(s)] (FIG. 13, graph E) and this inverse filter can be digitally implemented by methods familiar to those skilled in the art. H'(s) is the frequency response of the new HPF with lower cutoff frequency, nominally 0.05 Hz. The digital filter for H'(s) is digitally generated (F) and applied along with [1-H(s)] (FIG. 13, graph E), resulting in the frequency response displayed in FIG. 13, graph G. A high pass filter suitable for use in ECG circuits block 510 can be implemented in full or in part by software that can run on microprocessor 512.

Figure 14:
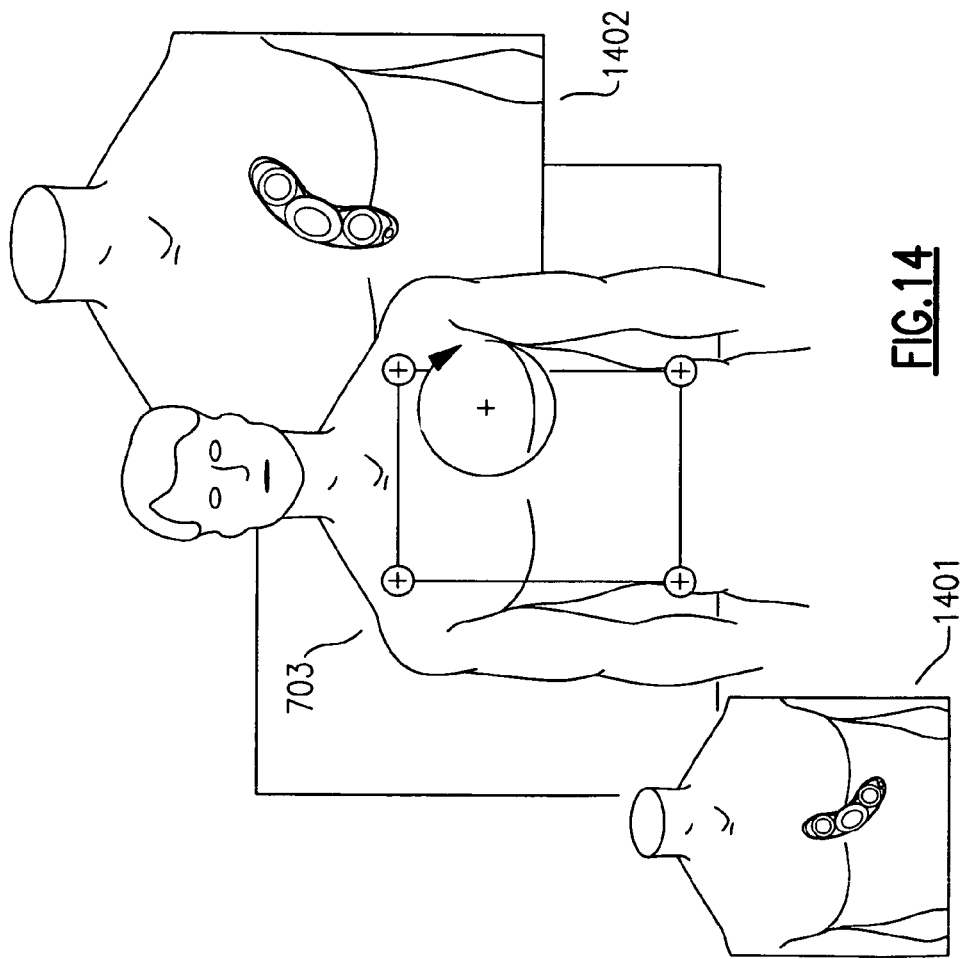
FIG. 14 shows two exemplary positions for a body worn ECG monitor to be non-permanently affixed directly to a patient's body.

FIG. 14 shows how a body worn monitor 100 configured as an ECG monitor can be situated on a patient in at least two different orientations to measure different heart vectors. A primary heart vector is measured by orientation from the patient's right shoulder to the left hip, as shown by position 1401. An alternative position 1402 can be more suitable where there is injury or where patient anatomy is such that it causes the preferred position 1401 to be less desirable. Also, body worn monitor 100 can be affixed to the side of patient 703 (similar to a measurement made by a conventional ECG "V" lead) or back of a patient 703 (such as where a patient needs to sleep on their stomach) to monitor still other ECG vectors (not shown). In effect, a body worn monitor 100 can be placed to pick a particular vector that can be traversed by the electrodes 109. For example at least the first three primary heart vectors, i.e. I, II, and III, can be made conveniently available in this manner.

While illustrated with an internal battery, it is important to note that a body worn physiological monitor 100 can be powered by either an internal power source only, an external power source only, or by an internal or an external power source. An internal power source can be a renewable power source, such as a rechargeable battery.

Another type of internal power source is a Peltier device operated in reverse, also called a Seebeck device. Seebeck discovered that a conductor generates a voltage when subjected to a temperature gradient. Thermoelectric couples are solid-state devices capable of generating electrical power from a temperature gradient, known as the Seebeck effect. (By contrast, the Peltier effect refers to the situation where electrical energy is converted into a temperature gradient.) A Seebeck device "couple" consists of one N-type and one P-type semiconductor pellet. The temperature differential causes electron flow from hot to cold in the N-type couple and hole flow from hot to cold in the P-type couple. To create an electromotive force (EMF), the following connections are made: On the cold side (i.e. the side that is exposed to room temperature) the pellets are joined and on the hot side (i.e. the patient side), the pellets are connected to a load, such as the computation and communication module 102. The open circuit voltage of a Seebeck device is given by $V=S \Delta T$, in which S is the Seebeck coefficient in volts/° K and $\Delta T$ is the temperature difference between the hot and cold sides. It is a challenge today to completely power the computation and communication module 102 from a Seebeck device that is of the same size as the computation and communication module 102. Presently, a Seebeck device may only provide supplementary power, but as electronics migrate toward lower power and Seebeck coefficients and thermocouple densities improve, a Seebeck device can be a viable long-term power solution for a patient-worn monitor. Other methods of generating energy, such as mechanical (as is used in some wrist watches) and solar, can also be viable methods for providing a renewable self-contained power source for a body worn monitor.

Turning to analysis routines suitable for use on a body worn monitor, typically, ECG beat picking, such as by using wavelet or Fourier transforms and/or matched filter analysis in the time domain can be computationally expensive. Modeling the QRS pulse as three triangles with alternating polarities creates a rough matched filter for the QRS pulse. Taking the second derivative results in impulse functions at the peaks of the triangles (where the first derivative is discontinuous), and all other points are zero. The second derivative method also makes the convolution with incoming data extremely efficient as most of the multiplies have a 0 as the multiplicand and requires minimal computation. The result can then be integrated twice to produce a matched-filter output, which can be fed into the beat-picking algorithm that provides fiducial marks. Using a second matched filter that is sinusoidal in shape and with appropriate discriminators, the system can provide indications of Life Threatening Arrhythmias (LTA); that is, Asystole, Vfib, and Vtach. While the accuracy of this system is less competitive with a high-end Arrhythmia solutions such as those provided, for example, by Mortara, the filters can be tuned to err toward false positives and upon a positive LTA response, activate transmission of full waveforms.

Research has also shown that analysis of the R-R portion of the ECG waveform interval statistics can provide a method to predict atrial flutter. Applying this and other low-computational cost methods can allow a body worn monitor device to begin transmitting full waveforms for either clinical or algorithmic analysis by a more powerful engine, when the probability of other arrhythmias is high. Transmitting only the R-R intervals of ECG waveforms is an example of a lossy data compression method. R-R intervals comprise a string of data and the string of data can also be compressed. Lossless or lossy data compression of the entire waveform can be implemented to save battery life, including not transmitting (or perhaps not even sampling) data between the T and the P wave. Because data compression results in less data to transmit, the power saved may offset the computation cost of the data compression.

While we have referred often to ECG applications herein, the application of low-intensity computational methods as a power saving measure apply equally well to other types of low power-sensors, including, but not limited to EEG, $SPO_2$, temperature, and invasive or non-invasive blood pressure measurements. Whether the body-worn medical-grade monitor performs complex analysis or simply compares a single numeric value to a single numeric limit, the device can function in a low-power radio state until a predetermined threshold is exceeded. A body worn monitor can also periodically send data or send data upon external request. Additionally, external devices can send commands to modify the operating parameters and thresholds.

Turning to other communication matters, it may be that adverse events occur in which no uplink is available. In a case of no uplink (failed communications), the body worn monitor can buffer time-stamped waveforms corresponding to any adverse events. The buffers can also store waveforms for later analysis in which this storage is triggered by the patient when the patient recognizes a condition, such as chest pain. In the case of an alarm that occurs when there is no uplink, alarms can be configured to be latched until confirmed by a clinician. Preferably, non-continuous data are marked (time stamp, sample number) to allow correlation of non-continuous data with continuous data and data are also marked to indicate when an alarm was initiated for later data analysis, including algorithm performance analysis.

In those instances in which many body worn monitor devices are used in close proximity to one another, there can be concern that the reports from one body worn monitor might be interchanged with reports from another body worn monitor. The body worn monitor presented herein, can be configured with a patient context (i.e. name, room number, patient ID, age, etc) and can maintain that context for as long as the monitor is connected to the patient to avoid such problems. The body worn monitor can determine the status of its connection to the patient via a continuous vital signs monitor, pressure, temperature, galvanic response, or similar input. Upon detection of a loss of connection with a patient, the device can, depending upon different variable settings, either erase the patient context or when re-connected to the patient, require the care giver to confirm the patient context. When the body worn monitor is initially powered up or connected to a patient, it can have a time holdoff for alarms to prevent false alarms (e.g. low heart rate, lead-fail detection) while the system stabilizes.

Regarding firmware updates, where there are large numbers of body worn monitors in a hospital, it can be problematic to keep them all updated with the latest version of firmware. One solution to this problem is to provide a wireless update ability for downloading and installing new firmware and/or configurations into all of the body worn monitors.

While the present invention has been particularly shown and described with reference to the preferred mode as illustrated in the drawings, it will be understood by one skilled in the art that various changes in detail may be effected therein without departing from the spirit and scope of the invention as defined by the following claims. It is further understood that several aspects of the invention, including, but not limited to, defibrillation protection resistors, pacer detect circuit disabling, methods for ECG signal high pass filtering, and various other low power modes are not limited to body worn monitors, and can be used in ECG monitors of any type.

We claim:

1. A body worn patient monitoring device comprising:
   a disposable module including a plurality of electrical connections, said electrical connections adapted to be couplable to a skin surface to measure physiological signals, at least one of said electrical connections comprising a half cell, the disposable module including a disposable module connector;
   a power source to power the body worn patient monitoring device;
   a communication-computation module being removable and reusable, having a communication-computation module connector to receive physiological signals from the disposable module via said disposable module connector, the communication-computation module including:
      a microprocessor to actively monitor the patient and to perform a real-time physiological analysis of the physiological signals, said analysis determining an occurrence of a predetermined physiological event, and
      a radio circuit to communicate, upon determination of the predetermined physiological event, a result of the physiological analysis on the occurrence of the predetermined physiological event, via a radio transmission to a remote radio receiver, wherein the disposable module is mechanically and electrically coupled directly to the communication-computation module and the body worn patient monitoring device including the disposable module and the communication-computation module is adapted to be directly non-permanently affixed to the skin surface of the patient; and
   at least one series current-limiting resistor configured to protect the communication-computation module, the at least one series current-limiting resistor being screened on a flexible substrate, the at least one series current-limiting resistor being in the form of resistive traces.

2. The body worn device of claim 1, wherein the plurality of electrical connections to the body comprise at least one of direct electrical connections to the body and indirect electrical connections to the body.

3. The body worn device of claim 2, wherein the indirect electrical connections to the body comprise capacitive connections to the body.

4. The body worn device of claim 1, wherein the body worn patient monitoring device comprises an ECG monitor and at least two of the electrical connections are ECG electrodes.

5. The body worn device of claim 4, wherein the ECG electrodes comprise a material screened onto the flexible substrate.

6. The body worn device of claim 5, wherein the at least one series current-limiting resistor protects the communication-computation module during a patient defibrillation event.

7. The body worn device of claim 4, wherein the mechanical interface from the at least one series current-limiting resistor to the EGG electrode includes a filleted edge.

8. The body worn device of claim 4, wherein the mechanical interface from the at least one series current-limiting resistor to the EGG electrode comprises overlapped layers.

9. The body worn device of claim 8, wherein the overlapped layers comprise a carbon resistive layer screened over a conductive surface, the carbon resistive layer having substantially the same shape as the conductive surface.

10. The body worn device of claim 1, further comprising an insulating material overlaying the at least one series current-limiting resistor to prevent arcing.

11. The body worn device of claim 5, wherein the EGG electrodes are formed substantially in the shape of an annulus.

12. The body worn device of claim 11, wherein the annulus comprises a conductive link.

13. The body worn device of claim 5, wherein the substrate is shaped to allow placement on the patient to monitor at least one of a set of standard ECG vectors while simultaneously reducing motion and muscle artifact in the corresponding ECG vector signal.

14. The body worn device of claim 1, wherein the power source is a renewable power source internal to the body worn device.

15. The body worn device of claim 1, wherein the power source comprises a rechargeable battery or a one time use battery.

16. The body worn device of claim 1, wherein the power source is a battery contained within said disposable module.

17. The body worn device of claim 1, wherein the power source is a Seebeck device.

18. The body worn device of claim 1, wherein one of the electrical connections is a reference electrode that can be used to improve common mode rejection (CMR).

19. The body worn device of claim 1, further comprising a virtual electrode as a reference electrode to improve CMR.

20. The body worn device of claim 19, wherein the virtual electrode is an electrode adapted to be situated near the skin of the patient, but not directly connected to the skin.

21. The body worn device of claim 19, wherein the virtual electrode is adapted to include a capacitive coupling of a body of the communication-computation module to the skin surface of the patient to reduce power line frequency interference.

22. The body worn device of claim 19, including a reference electrode switch for selectively choosing between using the virtual electrode as the reference electrode and a directly connected electrode as the reference electrode and wherein when the reference electrode switch selects the virtual electrode, the directly connected electrode can be used as an additional ECG electrode.

23. The body worn device of claim 19, wherein the reference electrode is a passive electrical connection or the reference electrode is actively driven.

24. The body worn device of claim 1, wherein the communication-computation module includes a pacer detection circuit.

25. The body worn device of claim 24, wherein the pacer detection circuit generates a microprocessor interrupt to inform the microprocessor that a pacer event occurred.

26. The body worn device of claim 25, wherein the microprocessor interrupt is used to mark a corresponding physiological signal in time as related to a pacer event.

27. The body worn device of claim 25, wherein the device automatically determines if a patient has a pacemaker and only enables the pacer detect circuit when a pacemaker is present.

28. The body worn device of claim 25, wherein the device is configured by an external input to enable or disable the pacer detect circuit.

29. The body worn device of claim 1, wherein the body worn device includes circuit protection to allow the device to survive multiple defibrillation cycles of at least 360 joules.

30. The body worn device of claim 29, wherein the circuit protection comprises a gas discharge tube or a plurality of diodes to clamp or limit the signals from the electrical connections.

31. The body worn device of claim 29, wherein a plurality of components of the circuit protection are distributed between the disposable module and the communication-computation module.

32. The body worn device of claim 1, further comprising a high pass filter with a selectable corner frequency to filter the physiological signals.

33. The body worn device of claim 32, wherein the corner frequency is selected by a switch selectable resistance.

34. The body worn device of claim 32, wherein the corner frequency is selected by one or more switching capacitors switched a rate higher than the corner frequency of a low pass anti-aliasing filter.

35. The body worn device of claim 32, wherein the high pass filter is implemented in software running on the microprocessor.

36. The body worn device of claim 1, wherein the body worn device self checks a pacer detection circuit by injecting a simulated pacer pulse into a front end amplifier to stimulate the pacer detection circuit by simulating the presence of a patient's pacemaker.

37. The body worn device of claim 1, wherein the communication-computation module includes circuit components configured to detect failure of contact of one or more of the electrical connections with the skin surface of the patient.

38. The body worn device of claim 1, wherein the communication-computation module is protected from external high energy signals by electro-surgical isolation suppression circuits.

39. The body worn device of claim 1, wherein an algorithm running on a microprocessor in the body worn device causes the body worn device to enter a low power mode that disables at least one circuit of the body worn device, from the end of a "T wave" at the end of one heart beat to the beginning of a "P wave" at the beginning of the next heart beat, to save power.

40. The body worn device of claim 4, including an ESIS filter having a low enough corner frequency such that the energy from a pacer pulse is recorded by at least one sample, even though the pacer pulse itself is of small duration compared to the sample rate and the pacer pulse occurs between samples.

41. The body worn device of claim 1, wherein neon bulbs connected from the physiological sensors to an electronics common (ground) protect one or more internal circuits of the communication-computation module from a defibrillation pulse.

42. The body worn device of claim 1, wherein a plurality of diodes disposed between the physiological sensors and an electronics common (ground) protect one or more internal circuits of the communication-computation module from a defibrillation pulse.

43. The body worn device of claim 1, wherein the radio circuit communicates an unprocessed physiological signal.

44. The body worn device of claim 1, wherein the radio circuit communicates a result of the physiological analysis at a predetermined time.

45. A body worn patient monitoring device comprising:
a disposable module including a plurality of electrical connections, the electrical connections adapted for electrical coupling to a skin surface to receive physiological signals, the disposable module including a disposable module connector;
a power source to power the body worn patient monitoring device;
a communication-computation module, having a communication-computation module connector to receive the physiological signals from the disposable module via the disposable module connector, the communication-computation module including:
a microprocessor to actively monitor a patient and to perform a real-time physiological analysis of the physiological signals, the analysis determining an occurrence of a predetermined ECG event,
a radio circuit to communicate an unprocessed physiological signal or a result of the physiological analysis, at a predetermined time or on an occurrence of a predetermined event, via a radio transmission to a remote radio receiver, and
wherein the disposable module has a mechanical and electrical coupling to the communication-computation module, forming the body worn patient monitoring device as a single unit that is adapted to be directly and non-permanently affixed to the skin surface of the patient; and
at least one series current-limiting resistor configured to protect the communication-computation module, the at least one series current-limiting resistor being screened on a flexible substrate, the at least one series current-limiting resistor being in the form of resistive traces.

* * * * *